United States Patent [19]

Bissett et al.

[11] Patent Number: 4,847,072
[45] Date of Patent: Jul. 11, 1989

[54] PHOTOPROTECTION COMPOSITIONS COMPRISING TOCOPHEROL SORBATE

[75] Inventors: Donald L. Bissett, Hamilton; Rodney D. Bush, Cincinnati, both of Ohio

[73] Assignee: The Procter & Gamble Company, Cincinnati, Ohio

[21] Appl. No.: 112,574

[22] Filed: Oct. 22, 1987

[51] Int. Cl.⁴ .............................................. A61K 7/40
[52] U.S. Cl. ...................................... 424/59; 514/724
[58] Field of Search .......................... 424/59; 549/408; 514/724

[56] References Cited

U.S. PATENT DOCUMENTS 4,478,853 10/1984 Chaussee ............................. 424/358
4,663,157 5/1987 Brock .................................... 424/59

FOREIGN PATENT DOCUMENTS

0166221A2 2/1986 European Pat. Off. .............. 424/59

Primary Examiner—Joseph L. Schofer
Assistant Examiner—Jeffrey T. Smith
Attorney, Agent, or Firm—Milton B. Graff, IV; Gretchen R. Hatfield; Steven J. Goldstein

[57] ABSTRACT

Disclosed are pharmaceutical compositions comprising tocopherol sorbate which are useful for topical application to prevent damage to skin caused by acute or chronic UV exposure. Combinations of tocopherol sorbate and sunscreening agents are also disclosed.

Also disclosed is a method for using these compositions topically, to prevent damage to skin caused by acute or chronic UV exposure.

40 Claims, No Drawings

PHOTOPROTECTION COMPOSITIONS COMPRISING TOCOPHEROL SORBATE

TECHNICAL FIELD

This invention relates to topical compositions useful for protecting the skin from the harmful effects of ultraviolet irradiation, such as sunburn and sun-induced premature aging of the skin.

BACKGROUND OF THE INVENTION

Sunbathing is a popular activity worldwide. A suntan is associated with health, beauty, status and wealth. Many leisure-time activities, such as swimming, tennis, golf, and fishing, are done in the sun. Furthermore, many people are forced to be in the sun for long periods of time due to their occupation.

However, the damaging effects of sunlight on skin are well documented. Contrary to what most people believe, it is not necessary that one sunbathe to suffer the ill-effects of excessive UV exposure. In fact, a lot of damage can be done just by routine day-to-day activities in the sunlight. Some scientists estimate that over 70 percent of the damage the sun inflicts on the average person's skin over a lifetime is the result of simply being outdoors or even sitting by a window.

The major short term hazard of prolonged exposure to sunlight is erythema (i.e., sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard of erythema, there are also long term hazards associated with UV radiation exposure. One of these long term hazards is malignant changes in the skin surface. Numerous epidemiologic studies demonstrate a strong relationship between sunlight exposure and human skin cancer. Another long term hazard of ultraviolet radiation is premature aging of the skin. This condition is characterized by wrinkling and yellowing of the skin, along with other physical changes such as cracking, telangiectasis (spider vessels), solar ketatoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed, Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, DePolo, issued June 7, 1983; the disclosures of all of which are incorporated herein by reference. Hence, although the immediate effects of ultraviolet radiation may be cosmetically and socially gratifying, the long-term hazards are cumulative and potentially serious.

The fact that these effects are taken seriously by the general public is suggested by considering the sun protection products' market. This market has grown considerably in recent years and many new products are introduced each year. What used to be looked upon as a seasonal business is no longer. Sun protection compounds are now included in a diversity of personal care products, particularly cosmetic-type products which are worn on a daily basis.

Obviously the most effective way to avoid excessive UV exposure is to simply refrain from being out in the sun. This is not only an impractical solution but an impossible one for those who work out-of-doors. Furthermore, some effects of exposure to sunlight are beneficial. Vitamin D is synthesized in skin exposed to UV radiation. A deficiency of this vitamin in the body can cause rickets or osteomalacia. Also, recent research suggests that sunlight can alter physical processes in ways that could enhance one's feeling of well-being.

Sunscreening agents exist naturally in the skin. These include melanin, carotenoids, urocanic acid, proteins and lipids. These natural sunscreens do not afford complete protection however, and for persons with very light skin they afford little protection at all.

Over the years, many means have been conceived of to mitigate the effects of UV-exposure. In Middle Eastern countries people shield their skin with long robes, kaffiyehs and veils. This is not an acceptable solution for most people however.

Sunblock agents are commercially available to protect the skin from UV radiation. These agents scatter or reflect ultraviolet radiation. Examples include titanium dioxide and zinc oxide. However, compositions containing these agents are opaque, generally unattractive in color, and are viewed as unacceptable for usage on more than just the nose or tops of the ears. Furthermore, these agents are very susceptible to rub-off or wear-off resulting in little or no protection.

Another type of agent available is one which provides a "tan" without exposure to the sun. Such agents generally consist of a skin dye and in no way protect against harmful UV-irradiation. These agents are applied to the skin wherever the appearance of a tan is desired. One example is dihydroxyacetone, which provides color through a reaction with specific amino acids in the stratum corneum. A drawback of this type of product is that it results in uneven coloration and a somewhat unnatural reddish-brown hue.

Related to these products are artifical tanning compounds which are taken orally. One example is canthaxanthin. These compounds apparently work by coloring the fat cells under the epidermal layer. Such products also result in uneven tanning and require continual maintenance doses. Again, these products provide no protection against harmful irradiation.

The most common agents for sun protection are sunscreens. These agents exert their effects through chemical means, i.e., they absorb ultraviolet radiation so that it cannot penetrate the skin. Sunscreens present the user with several problems. For example, they must be on the surface of the skin at the time of exposure to be effective. Sunscreens are preventative so one must anticipate being in the sun. to be most effective, sunscreens must be on the skin as a continuous uniform film. Delivering such a film to the surface of the skin is very difficult; maintaining the film over time is almost impossible. Sunscreens must remain on the *surface* of the skin during exposure. However, sunscreens are easily rubbed off or washed off by sweating or swimming and can also be lost by penetration into the skin. Sunscreening agents often cause irritation to the skin and eyes, primarily burning or stinging, respectively. Another problem with sunscreens is that the greater their efficacy, the more the tanning response is decreased.

Methods have been suggested for improving the look of skin after the UV-induced damage has occurred. Topical application of collagen as a moisturizing agent is one such method. Others involve injections of collagen or dimethylpolysiloxane. Yet another procedure entails the application of a chemical preparation to the skin to effect a "chemical peel".

Alternatively, methods have been suggested for repairing skin after UV-induced damage has occurred. One such method involves application of retinoic acid to the skin as disclosed in U.S. Pat. No. 4,603,146, Kligman, issued July 29, 1986. None of these procedures have been proven to be fully effective and most involve extensive and costly treatment. Clearly, it would be far better to prevent the damage induced by UV-irradiation *before* it occurs. A photo-protecting agent which protects against both short-term and long-term UV-damage to the skin while, at the same time, allows for tanning of the skin in a safe, convenient manner would be most ideal.

Tocopherol (Vitamin E) has been disclosed for use as a photoprotector in topical compositions. See, e.g., U.S. Pat. No. 4,144,325, Voyt, issued Mar. 13, 1974. Tocopherol works to protect the skin from deleterious effects of UV-irradiation without interfering with the tanning response. However, cosmetic industry experience suggests that tocopherol may have stability problems, specifically oxidation problems. One frequently used approach to address these problems involves the formulation of compositions including esters of tocopherol, these esters generally being more stable than tocopherol itself. U.S. Pat. No. 4,248,861, Schutt, issued Feb. 3, 1981, discloses the use of tocopherol acetate, tocopherol succinate, tocopherol propionate, and tocopherol oleate for preventing deleterious effects to skin of solar radiation. U.S. Pat. No. 4,000,276, Hasunuma et al., issued Dec. 28, 1976, discloses a cosmetic compositions comprising tocopherol orotate. Tocopherol benzoate, p-aminobenzoate, and p-nitro-benzoate have been disclosed for use in sunscreen compositions in European Patent Application No. 166,221, Tuominen, published Jan. 2, 1986. The linoleate, nicotinate, and 2-ethylhexanoate esters of tocopherol have been disclosed for use in cosmetic compositions in Japanese Laid-Open Application No. 61-143,331, published Dec. 14, 1984. Increased formulational stability, as provided by most tocopherol esters, unfortunately comes at the cost of decreased photoprotection efficacy. Clearly, a photoprotecting agent which works as well as tocopherol but which is not subject to stability problems would be most desirable.

The topical use of anti-inflammatory agents to alleviate erythema is known. Compositions containing steroidal anti-inflammatories, non-steoidal anti-inflammatories, as well as "natural" anti-inflammatories, such as an extract of the plant *Aloe vera*, have been disclosed for such use. See e.g., U.S. Pat. No. 4,185,100, Rovee, issued Jan. 22, 1980 (hydrocortisone, dexamethasone, naproxen, ketoprofen, ibuprofen); U.S. Pat. No. 4,338,293, Holick, issued July 6, 1982, (steroidal anti-inflammatories); Law, et al., *Br. J. Pharmac.*, 59(4), 591–597 (1977) ibuprofen); Kaidbey, *J. Invest, Dermatology*, 66, 153–156 (1976) (indomethacin); and Gruber, et al., *Clinical Pharm. and Therapeut.*, 13(1), 109–113 (1971) (aspirin, fenoprofen). Short-term application of anti-inflammatory agents prior to UV exposure to prevent erythema, as well as application after UV exposure to lessen UV-induced damage to skin, has been taught.

It is an object of the present invention to provide a topical composition in a stable form, the use of which will prevent both acute (erythema) and chronic (photoaging) effects of exposure to the sun.

It is also an object of the present invention to provide a topical composition, a cleansing composition, and a method for preventing these deleterious effects of the sun without interfering with the tanning response.

It is further an object of the present invention to provide a photoprotection composition which penetrates into the skin and which is less susceptible to rub-off, wear-off or wash-off.

It is a still further object of the present invention to provide a photoprotection composition which can be applied to the skin in advance of UV exposure without significant loss of efficacy.

SUMMARY OF THE INVENTION

The present invention relates to a composition useful for topical application comprising a photoprotectively effective amount of tocopherol sorbate and a safe and effective amount of a topical carrier.

The present invention also relates to a composition useful for topical application comprising a photoprotectively effective amount of tocopherol sorbate, a photoprotectively effective amount of a sunscreening agent, and a safe and effective amount of a topical carrier.

The present invention further relates to a method of inhibiting the deleterious effects of ultraviolet light exposure to skin comprising applying a safe and photoprotectively effective amount of tocopherol sorbate to the skin in conjunction with exposing the skin to ultraviolet light.

The present invention further relates to a method of inhibiting the deleterious effects of ultraviolet light exposure to skin comprising applying a safe and photoprotectively effective amount of tocopherol sorbate and a safe and photoprotectively effective amount of a sunscreening agent to the skin in conjunction with exposing the skin to ultraviolet light.

DETAILED DESCRIPTION OF THE INVENTION

Active Agent

The present invention relates to the topical use of compositions containing tocopherol sorbate to prevent the deleterious effects of UV exposure. Tocopherol sorbate is the tocopherol (more commonly known as Vitamin E) ester of sorbic acid.

Tocopherol sorbate can be synthesized by standard esterification methods known in the art. Any of the tocopherols are suitable for esterification, including the monomethyl, dimethyl or trimethyl derivatives of tocol. More specifically any of alpha tocopherol (5,7,8-trimethyl tocol), beta tocopherol (5,8-dimethyl tocol), gamma tocopherol (7,8-dimethyl tocol), delta tocopherol (8-methyl tocol), epsilon tocopherol (5-methyl tocol), zeta tocopherol (5,7-dimethyl tocol), and eta tocopherol (7-methyl tocol) may be used to make tocopherol sorbate. Some of these isomers may be more efficacious for photoprotection than others. The beta, gamma and delta tocopherols exhibit particularly strong anti-oxidant properties and thus may be preferred for making the photoprotectors of the present invention. Mixtures of these isomers may also be used to make the tocopherol sorbate useful for the present invention.

Tocopherol sorbate may be made, for example, by first combining one mole of di-alpha-tocopherol with about 4.3 moles of polyphosphate ester. One mole of sorbic acid is then added to the reaction mixture and the solution is stirred for about 16 hours. The sample is washed with an equal volume of deionized water and an equal volume of diethylether is added. The layers are separated and the organic layer is washed with 8.7 liters of sodium bicarbonate (1 kg/12 l of water). Four liters of anhydrous ether are added to achieve separation of the phases. The organic layer is dried over 1 kg of sodium sulfate, anhydrous. The organic fraction is decanted from sodium sulfate and dried by rotoevaporation at about 50° C. and about 30 mm Hg to give about 574 grams. The sample is washed with one liter of hexanes to remove any solid or residual chloroform. The sample is dried to yield about 500 g of a yellow/brown viscous oil of greater than 99% purity.

A safe and photoprotectively effective amount of tocopherol sorbate is used in the compositions of the present invention. By "safe and photoprotectively effective" amount is meant an amount sufficient to provide photoprotection when the composition is properly applied, but not so much as to cause any side effects or adverse skin reactions; generally from about 1% to about 20%, preferably from about 2% to about 10%, of the composition.

It is important to note that tocopherol sorbate is a non-sunscreen photoprotecting agent. A sunscreen works on the surface of the skin to absorb UV radiation so that the harmful rays never enter the skin. Tocopherol sorbate works in the skin, perhpas by its radical scavenging and photochemical reaction quenching capabilities which prevent damaging reactions in the skin. Because tocopherol sorbate penetrates the skin to work, rub-off, wear-off or wash-off of the active, which lessen efficacy for sunscreens considerably, are essentially irrelevant with the present invention. Furthermore, though critical with a sunscreen, it is not necessary to keep an even coating of the active of the present invention on the skin for the entire exposure period. Tocopherol sorbate can be applied to the skin up to four hours or longer prior to UV exposure. Tocopherol sorbate protects against both acute effects of UV exposure, e.g., sunburn, and chronic effects of UV exposure, e.g., premature aging of the skin.

As a radical scavenger the topical use of tocopherol sorbate may also be beneficial to people with extreme sensitivity to sunlight. Such use may enable individuals with these skin disorders to tan.

Carriers

In addition to the active agent, tocopherol sorbate, the compositions of the present invention contain a safe and effective amount of an acceptable carrier. The term "acceptable topical carrier" encompasses both pharmaceutically-acceptable carriers and cosmetically-acceptable carriers, and it encompasses substantially non-irritating compatible components (either taken alone or in mixtures) which are suitable for delivering the active component to the skin. The term "compatible", as used herein, means that the components of the carrier must be capable of being commingled with tocopherol sorbate, and with each other, in a manner such that there is no interaction which would substantially reduce the efficacy of the composition during use for protecting the skin from the effects of UV radiation. These carriers must, of course, be of sufficiently high purity and sufficiently low toxicity to render them suitable for chronic topical administration to the skin of humans or lower animals. The term "safe and effective amount" of carrier means an amount sufficient to deliver the tocopherol sorbate to the skin but not so much as to cause any side effects or skin reactions, generally from about 50% to about 99%, preferably from about 90% to about 98%, of the composition.

Variations in formulation of these carriers will result in a wide variety of products which fall within the scope of the present invention. These product types can be divided into two classes: pharmaceutical/cosmetic compositions and cleaning compositions.

Pharmaceutical/Cosmetic Compositions

The pharmaceutical/cosmetic compositions of the present invention may be made into a wide variety of product types. These include, for example, lotions, creams, beach oils, gels, sticks, sprays, ointments, pastes, mousses and cosmetics. These product types may comprise either of two basic types of carrier systems, i.e., solutions and emulsions.

the pharmaceutical/cosmetic compositions of the present invention formulated as solutions typically include a pharmaceutically- or cosmetically-acceptable organic solvent. The terms "pharmaceutically-acceptable organic solvent" and "cosmetically-acceptable organic solvent" refer to an organic solvent which, in addition to being capable of having dispersed or dissolved therein the tocopherol sorbate, also possesses acceptable safety (e.g. irritation and sensitization characteristics), as well as good aesthetic properties (e.g., does not feel greasy or tacky). The most typical example of such a solvent is isopropanol. Examples of other suitable organic solvents include: propylene glycol, polyethylene glycol (200–600), polypropylene glycol (425–2025), glycerol, 1,2,4-butanetriol, sorbitol esters, 1,2,6-hexanetriol, ethanol, butanediol, water and mixtures thereof. These solutions contain from about 1% to about 20%, preferably from about 2% to about 10%, of tocopherol sorbate, and from about 80% to about 99%, preferably from about 90% to about 98%, of an acceptable organic solvent.

If the pharmaceutical/cosmetic compositions of the present invention are formulated as an aerosol and applied to the skin as a spray-on, a propellant is added to a solution composition. Examples of propellants useful herein include the chlorinated, fluorinated and chlorofluorinated lower molecular weight hydrocarbons. Other propellants useful in the present invention include lower molecular weight hydrocarbon mixtures (e.g., the mixture of butane, isobutane and propane known commercially as Propellant A46, made by Phillips Chemical Co., a subsidiary of Phillips Petroleum Company), ethers and halohydrocarbons such as dimethyl ether or dichlorodifluoromethane alone or mixtures thereof with cichlorotetrafluoroethane. Mixtures of hydrocarbon and halohydrocarbon propellants and nitrous oxide may also be used. Nitrogen and carbon dioxide can also be used as propellant gases. They are used at a level sufficient to expel the contents of the container. A more complete disclosure of propellants useful herein can be found in Sagarin, *Cosmetics Science and Technology*, 2nd Edition, Vol. 2, pp. 443–465 (1972), incorporated herein by reference.

Alternatively, emollients may comprise the carrier system of the present invention formulated as a solution. An example of a composition formulated in this way would be a beach oil product. Such compositions contain from about 1% to about 20% of tocopherol sorbate and from about 2% to about 50% of a pharmaceutically/cosmetically-acceptable emollient.

As used herein, "emollients" refer to materials used for the prevention or relief of dryness, as well as for the protection of the skin. A wide variety of suitable emollients are known and may be used herein. Sagarin, *Cosmetics, Science and Technology*, 2nd Edition, Vol. 1, pp,. 32-43 (1972), incorporated herein by reference, contains numerous examples of suitable materials. Examples of classes of useful emollients include the following:

1. Hydrocarbon oils and waxes. Examples include mineral oil, petrolatum, paraffin, ceresin, ozokerite, microcrystalline wax, polyethylene, and perhydrosqualene.
2. Silicone oils, such as dimethyl polysiloxanes, methylphenyl polysiloxanes, water-soluble and alcohol-soluble silicone glycol copolymers.
3. Triglyceride esters, for example vegetable and animal fats and oils. Examples include castor oil, safflower oil, cottonseed oil, corn oil, olive oil, cod liver oil, almond oil, avocado oil, palm oil, sesame oil, and soybean oil.
4. Acetoglyceride esters, such as acetylated monoglycerides.
5. Ethoxylated glycerides, such as ethoxylated glyceryl monostearate.
6. Alkyl esters of fatty acids having 10 to 20 carbon atoms. Methyl, isopropyl, and butyl esters of fatty acids are particularly useful herein. Examples of other useful alkyl esters include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.
7. Alkenyl esters of fatty acids having 10 to 20 carbon atoms. Examples include oleyl myristate, oleyl stearate, and oleyl oleate.
8. Fatty acids having 10 to 20 carbon atoms. Suitable examples include pelargonic, lauric, myristic, palmitic, stearic, isostearic, hydroxystearic, oleic, linoleic, ricinoleic, arachidic, behenic, and erucic acids.
9. Fatty alcohols having 10 to 20 carbon atoms. Lauryl, myristyl, cetyl, hexadecyl, stearyl, isostearyl, hydroxystearyl, oleyl, ricinoleyl, behenyl, and erucyl alcohols, as well as 2-octyl dodecanol, are examples of satisfactory fatty alcohols.
10. Fatty alcohol ethers. Ethoxylated fatty alcohols of 10 to 20 carbon atoms include the lauryl, cetyl, stearyl, isostearyl, oelyl, and cholesterol alcohols having attached thereto from 1 to 50 ethylene oxide groups or 1 to 50 propylene oxide groups.
11. Ether-esters such as fatty acid esters of ethoxylated fatty alcohols.
12. Lanolin and derivatives. Lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases are illustrative of emollients derived from lanolin.

13. Polyhydric alcohols and polyether derivatives. Propylene glycol, dipropylene glycol, polypropylene glycols 2000 and 4000, polyoxyethylene polyoxypropylene glycols, polyoxypropylene polyoxyethylene glycols, glycerol, sorbitol, ethoxylated sorbitol, hydroxypropyl sorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol (2-methyl-2,4-pentanediol), 1,3-butylene glycol, 1,2,6-hexanetriol, ethohexadiol USP (2-ethyl-1,3-hexanediol), $C_{15}-C_{18}$ vicinal glycol, and polyoxypropylene derivatives of trimethylolpropane are examples of this class of materials.

14. Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethlene polyol fatty acid ester, sorbitan fatty acid esters, and polyoxyethylene sorbitan fatty acid esters are satisfactory polyhydric alcohol esters for use herein.

15. Wax esters such as beeswax, spermaceti, myristyl myristate, stearyl stearate.
16. Beeswax derivatives, e.g. polyoxyethylene sorbitol beeswax. These are reaction products of beeswax with ethoxylated sorbitol of varying ethylene oxide content, forming a mixture of ether-esters.
17. Vegetable waxes including carnauba and candelilla waxes.
18. Phospholipids, such as lecithin and derivatives.
19. Sterols. Cholesterol and cholesterol fatty acid esters are examples thereof.
20. Amides such as fatty acid amides, ethoxylated fatty acid amides, solid fatty acid alkanolamides.

Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol. Preferred skin conditioning agents are the propoxylated glycerol derivatives disclosed in U.S. patent application Ser. No. 023,059, Orr et al., filed Mar. 6, 1987. These agents preferably have a formula selected from:

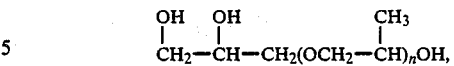

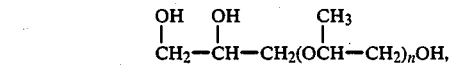

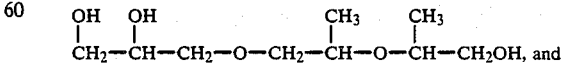

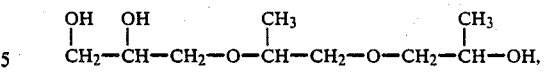

wherein n=1 or 2, and mixtures thereof. Preferably any of the compositions of the present invention comprise from about 1% to about 10% by weight of this propoxylated glycerol derivative.

A lotion can be made from a solution carrier system. Lotions typically comprise from about 1% to about 20%, preferably from about 2% to about 10%, tocopherol sorbate; from about 1% to about 20%, preferably from about 5% to about 10%, of an emollient; and from about 50% to about 90%, preferably from about 60% to about 80%, water. Another type of product that may be formulated from a solution carrier system is a cream. A cream of the present invention would comprise from about 1% to about 20%, preferably from about 2% to about 10%, tocopherol sorbate; from about 5% to about 50%, preferably from about 10% to about 20%, of an emollient, and from about 45% to about 85%, preferably from about 50% to about 75%, water.

Yet another type of product that may be formulated from a solution carrier system is an ointment. An ointment may comprise a simple base of animal or vegetable oils or semi-solid hydrocarbons (oleaginous). Ointments may also comprise absorption ointment bases which absorb water to form emulsions. Examples of such ointment bases include anhydrous lanolin and hydrophilic petrolatum. Emulsion ointment bases may be oil-in-water or water-in-oil emulsions. Ointment carriers may also be water soluble. Examples of such ointment carriers include glycol ethers, propylene glycols, polyoxyl stearates, and polysorbates. An ointment may also comprise from about 2% to about 10% of an emollient plus from about 0.1% to about 2% of a thickening agent. Examples of suitable thickening agents include: cellulose derivatives (e.g., methyl cellulose and hydroxy propylmethyl cellulose), synthetic high molecular weight polymers (e.g., carboxyvinyl polymer and polyvinyl alcohol), plant hydrocolloids (e.g., karaya gum and tragacanth gum), clay thickeners (e.g., colloidal magnesium aluminum silicate and bentonite), and carboxyvinyl polymers (Carbopols®—sold by B. F. Goodrich Company, such polymers are described in detail in U.S. Pat. No. 2,798,053, Brown, issued July 2, 1957, incorporated herein by reference). A more complete disclosure of thickening agents useful herein can be found in Sagarin, *Cosmetics, Science and Technology*, 2nd Edition, Vol. 1, pp. 72–73 (1972), incorporated herein by reference.

If the carrier system is formulated as an emulsion, from about 1% to about 10%, preferably from about 2% to about 5%, of the carrier system comprises an emulsifier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's *Detergents and Emulsifiers*, North American Edition, pages 317-324 (1986); the disclosures of which are incorporated herein by reference. Preferred emulsifiers are anionic or nonionic, although the other types may also be used.

Examples of useful nonionic emulsifiers include fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene glycol wherein the fatty acid moiety contains from 10 to 20 carbon atoms, fatty acid monoglycerides wherein the fatty acid moiety contains from 10 to 20 carbon atoms, diethylene glycol, polyethylene glycols of molecular weight 200 to 6000, propylene glycol of molecular weight 200 to 3000, sorbitol, sorbitan, polyoxyethylene sorbitol, polyoxyethylene sorbitan and hydrophilic wax esters. Examples of such emulsifiers include polyoxyethylene (8) stearate, myristyl ethoxy (3) myristate, polyoxyethylene (100) monostearate, lauric diethanolamide, stearic monoethanolamide, hydrogenated vegetable glycerides, sodium stearoyl-2-lactylate and calcium stearoyl-2-lactylate.

Suitable anionic emulsifiers include the fatty acid soaps, e.g., sodium, potassium, and triethanolamine soaps, wherein the fatty acid moiety contains from 10 to 20 carbon atoms. Other suitable anionic emulsifiers include the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units.

Cationic emulsifiers useful in the present invention include quaternary ammonium, morpholinium and pyridinium compounds. Examples of such emulsifiers include dialkyl ($C_{12}$–$C_{18}$) quaternary ammonium salts, cetyl trimethyl ammonium salts; alkyl dimethyl benzyl ammonium salts, and cetyl pyridinium salts.

Single emulsion skin care preparations, such as lotions and creams, of the oil-in-water type and water-in-oil type are well-known in the cosmetic art and are useful in the present invention. Multiphase emulsion compositions, such as the water-in-oil-in-water type, as disclosed in U.S. Pat. No. 4,254,105, Fakuda et al., issued Mar. 3, 1981, herein incorporated by reference, are also useful in the present invention. In general, such single or multiphase emulsions contain water, emollients and emulsifiers as essential ingredients.

Triple emulsion carrier systems comprising an oil-in-water-in-silicone fluid emulsion composition as disclosed in U.S. patent application Ser. No. 022,876, Figueroa et al., filed Mar. 6, 1987, herein incorporated by reference, are also useful in the present invention. More particularly, such triple emulsion carrier systems comprise (a) from about 15% to about 90% by weight (of the vehicle) of a silicone fluid continuous phase consisting essentially of at least one liquid organopolysiloxane, (b) from about 30% to about 80% by weight (of the vehicle) of an aqueous discontinuous phase comprising an oil-in-water emulsion of a cosmetically-acceptable oily liquid non-particulate phase dispersed in an aqueous phase, and (c) from about 0.5% to about 5% by weight (of the vehicle) of an effective dispersing amount of dimethicone copolyol for dispersing (b) in (a).

Preferably said liquid organopolysiloxane consists of one or more volatile organopolysiloxanes selected from the group consisting of octamethylcyclotetrasiloxane, decamethylcyclopentasiloxane, dodecamethylcyclohexasiloxane, cyclomethicone, and hexamethyldisiloxane in a mixture with one or more non-volatile organopolysiloxanes selected from the group consisting of: dimethicone copolyol, dimethylpolysiloxane, diethylpolysiloxane, mixed $C_1$–$C_3$ alkyl polysiloxane, phenyl dimethicone and a high molecular weight dimethicone having an average molecular weight of from about 200,000 to about 1,000,000, in a respective weight ratio of from about 5:1 to about 25:1, and said oily phase comprises heavy mineral oil, cholesterol and cetyl palmitate in a respective weight ratio of about 10:5:1.

This triple emulsion carrier system can be combined with from about 1% to about 20%, preferably from about 2% to about 10%, tocopherol sorbate to yield the pharmaceutical/cosmetic composition of the present invention.

Another emulsion carrier system useful in the pharmaceutical/cosmetic compositions of the present invention is a microemulsion carrier system. Such a system comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens) or other nonionics; and from about 7% to about 20% water. This carrier system is combined with from about 2% to about 10% tocopherol sorbate.

Lotions and creams can be formulated as emulsions as well as solutions. Typically such lotions comprise from about 1% to about 20%, preferably from about 2% to about 10%, tocopherol sorbate; from about 1% to about 20%, preferably from about 5% to about 10%, of an emollient; from about 25% to about 75%, preferably from about 45% to about 95%, water; and from about 1% to about 10%, preferably from about 2% to about 5%, of an emulsifier. Such creams would typically comprise from about 1% to about 20%, preferably from about 2% to about 10%, tocopherol sorbate; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

If the pharmaceutical/cosmetic compositions of the present invention are formulated as a gel or a cosmetic stick, a suitable amount of a thickening agent as disclosed supra, is added to a cream or lotion formulation.

The pharmaceutical/cosmetic compositions of the present invention may also be formulated as makeup products, such as foundations or lipsticks. Foundations are solution or lotion-based with appropriate amounts of thickeners, pigments and fragrance. Lipsticks are composed essentially of an oil-wax base stiff enough to form a stick, with pigmentation dispersed therein.

The topical pharmaceutical/cosmetic compositions of the present invention may contain, in addition to the aforementioned components, a wide variety of additional oil-soluble materials and/or water-soluble materials conventionally used in topical compositions, at their art-established levels.

Among the optional oil-soluble materials are nonvolatile silicone fluids, such as polydimethyl siloxanes with viscosities ranging from about 10 to about 100,000 centistokes at 25° C. These siloxanes are useful to enhance skin feel and are available from Dow Corning Corporation as the Dow Corning 200 series. These optional oil-soluble materials may comprise up to about 20% of the total composition, preferably up to about 10%.

Various water-soluble materials may also be present in the compositions of this invention. These include humectants, such as glycerol, sorbitol, propylene glycol, alkoxylated glucose and hexanetriol, ethyl cellulose, polyvinyl alcohol, carboxymethyl cellulose, vegetable gums and clays such as Veegum ® (magnesium aluminum silicate, R. T. Vanderbilt, Inc.); proteins and polypeptides; preservatives such as the methyl, ethyl, propyl and butyl esters of hydroxybenzoic acid (Parabens—Mallinckrodt Chemical Corporation), EDTA, methylisothiazolinone and imidazolidinyl ureas (Germall 115—Sutton Laboratories); and an alkaline agent such as sodium hydroxide or potassium hydroxide to neutralize, if desired, part of the fatty acids or thickener which may be present. In addition, the topical compositions herein can contain conventional cosmetic adjuvants, such as dyes, opacifiers (e.g., titanium dioxide), pigments and perfumes.

The pharmaceutical/cosmetic compositions of the present invention may also include a safe and effective amount of a penetration enhancing agent. By "safe and effective amount" is meant an amount sufficient to enhance penetration of tocopherol sorbate into the skin but not so much as to cause any side effects or skin reactions, generally from about 1% to about 5% of the composition. Examples of useful penetration enhancers, among others, are disclosed in U.S. Pat. Nos. 4,537,776, Cooper, issued Aug. 27, 1985; 4,552,872, Cooper et al., issued Nov. 12, 1985; 4,557,934, Cooper, issued Dec. 10, 1985; 4,130,667, Smith, issued Dec. 19, 1978; 3,989,816, Rhaadhyaksha, issued Nov. 2, 1976; 4,017,641, DiGiulio, issued Apr. 12, 1977; and European patent application No. 0043738, Cooper et al., published Jan. 13, 1982. U.S. Pat. No. 4,537,776 teaches a penetration-enhancing vehicle consisting essentially of (a) N-(2-hydroxyethyl)-pyrrolidone and (b) a cell envelope disordering compound selected from methyl laurate, oleic acid, oleyl alcohol, monoolein, myristyl alcohol, and mixtures thereof, wherein component (a) and (b) are present in a ratio of (a):(b) of about 1:5 to about 500:1 by weight. U.S. Pat. No. 4,557,934 teaches a pharmaceutical composition comprising the penetration enhancing agent 1-dodecylazacycloheptan-2-one, and a penetration enhancing diol or cycloketo compound selected from the group consisting of: 1,2-propanediol, 1,3-propanediol, 1,2-butanediol, pyrrolidone; 1-(2-hydroxyethyl)azacyclopentan-2-one, and mixtures thereof. U.S. Pat. No. 4,130,667 describes a penetration enhancer comprising:

(a) at least about 0.1% by weight of a sugar ester selected from sucrose monooctanoate, sucrose monodecanoate, sucrose monolaurate, sucrose monomyristate, sucrose monopalmitate, sucrose monostearate, sucrose monooleate, and sucrose dioleate; and (b) at least about 0.1% by weight of a phosphine oxide compound selected from octyldimethyl phosphine oxide, nonyl dimethyl phosphine oxide, decyl dimethyl phosphine oxide, undecyl dimethyl phosphine oxide, dodecyl dimethyl phosphine oxide, 2-hydroxydecyl dimethyl phosphine oxide, 2-hydroxy undecyl dimethyl phosphine oxide, and 2-hydroxy dodecyl dimethyl phosphine oxide.

Sulfoxides may be used in some executions in place of the phosphine oxide.

Other conventional skin care product additives may also be included in the compositions of the present invention. For example, collagen, hyaluronic acid, elastin, hydrolysates, primrose oil, jojoba oil, epidermal growth factor, soybean saponins, mucopolysaccharides, and mixtures thereof may be used.

Various vitamins may also be included in the compositions of the present invention. For example, Vitamin A and derivatives thereof, Vitamin $B_2$, biotin, pantothenic acid, Vitamin D and mixtures thereof may be used.

Cleaning Compositions

The skin cleaning compositions of the present invention comprise, in addition to tocopherol sorbate, a cosmetically-acceptable surfactant. The term "cosmetically-acceptable surfactant" refers to a surfactant which is not only an effective skin cleanser, but also can be used without undue toxicity, irritation, allergic response, and the like. Furthermore, the surfactant must be capable of being commingled with tocopherol sorbate in a manner such that there is no interaction which would substantially reduce the efficacy of the composition for protecting the skin from the effects of UV radiation.

The skin cleaning compositions of the present invention contain from about 1% to about 25%, preferably from about 5% to about 10%, tocopherol sorbate, and from about 1% to about 90%, preferably from about 50% to about 85%, of a cosmetically-acceptable surfactant.

The physical form of the skin cleansing compositions is not critical. The compositions can be, for example, formulated as toilet bars, liquids, pastes, or mousses. Toilet bars are most preferred since this is the form of cleansing agent most commonly used to wash the skin.

The surfactant component of the compositions of the present invention is selected from anionic, nonionic, zwitterionic, amphoteric and ampholytic surfactants, as well as mixtures of these surfactants. Such surfactants are well-known to those skilled in the detergency art.

The most common type of anionic surfactants can be broadly described as the water-soluble salts, particularly the alkali metal salts, of organic sulfuric reaction products having in the molecular structure an alkyl radical containing from about 8 to about 22 carbon atoms and a radical selected from the group consisting of sulfonic acid and sulfuric acid ester radicals. Important examples of these surfactants are the sodium, ammonium or potassium alkyl sulfates, especially those obtained by sulfating the higher alcohols produced by reducing the glycerides of tallow or coconut oil; sodium or potassium alkyl benzene sulfonates in which the alkyl group contains from about 9 to about 15 carbon atoms, especially those of the types described in U.S. Pat. Nos. 2,220,099 and 2,477,383, incorporated herein by reference; sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid esters of the reaction product of one mole of a higher fatty alcohol (e.g., tallow or coconut oil alcohols) and about three moles of ethylene oxide; sodium or potassium salts of alkyl phenol ethylene oxide ether sulfates with about three moles of ethylene oxide; sodium or potassium salts of alkyl phenol ethylene oxide; sodium or potassium salts of alkyl phenol ethylene oxide ether sulfates with about four units of ethylene oxide per molecule and in which the alkyl radicals contain about 9 carbon atoms; the reaction product of fatty acids esterified with isethionic acid and neutralized with sodium hydroxide where, for example, the fatty acids are derived from coconut oil; sodium or potassium salts of fatty acid amide of a methyl taurine in which the fatty acids, for example, are derived from coconut oil; and others known in the art, such as those specifically set forth in U.S. Pat. Nos. 2,486,921, 2,486,922 and 2,396,278, incorporated herein by reference.

An important type of useful anionic surfactants are soaps. Soaps which can be used as the surfactant in the present compositions include alkali metal (e.g., sodium or potassium) soaps of fatty acids containing from about 8 to about 24, preferably from about 10 to about 20, carbon atoms. The fatty acids used in making the soaps can be obtained from natural sources such as, for instance, plant or animal-derived glycerides (e.g., palm oil, coconut oil, babassu oil, soybean oil, castor oil, tallow, whale oil, fish oil, grease, lard, and mixtures thereof). The fatty acids can also be synthetically prepared (e.g., by oxidation of petroleum stocks or by the Fischer-Tropsch process).

Alkali metal soaps can be made by direct saponification of the fats and oils or by the neutralization of the free fatty acids which are prepared in a separate manufacturing process. Particularly useful are the sodium and potassium salts of the mixtures of fatty acids derived from coconut oil and tallow, i.e., sodium and potassium tallow and coconut soaps.

The term "tallow" as used herein in connection with fatty acid mixtures refers to acids which typically have an approximate carbon chain length distribution of 2.5% $C_{14}$, 29% $C_{16}$, 23% $C_{18}$, 2% palmitoleic, 41.5% oleic and 3% linoleic acid (the first three fatty acids listed are saturated). Other mixtures wth similar distributions, such as the fatty acids derived from various animal tallows and lard, are also included within the term tallow. The tallow can also be hardened (i.e., hydrogenated) to convert part or all of the unsaturated fatty acid moieties to saturated fatty acid moieties.

The term "coconut oil" as used herein refers to fatty acid mixtures which typically have an approximate carbon chain length distribution of about 8% $C_8$, 7% $C_{10}$, 48% $C_{12}$, 17% $C_{14}$, 9% $C_{16}$, 2% $C_{18}$, 7% oleic, and 2% linoleic acid (the first six fatty acids listed being saturated). Other sources having similar carbon chain length distribution, such as palm kernel oil and babassu oil, are included with the term coconut oil.

Nonionic surfactants may be broadly defined as compounds produced by the condensation of alkylene oxide groups (hydrophilic in nature) with an organic hydrophobic compound, which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

For example, a well-known class of nonionic surfactants is commercially available under the trade name "Pluronic" marketed by the BASF Wyandotte Corporation. These compounds are formed by condensing ethylene oxide with a hydrophobic base formed by the condensation of propylene oxide with propylene glycol. The hydrophobic portion of the molecule which, of course, exhibits water-insolubility has a molecular weight of from about 1500 to about 1800. The addition of polyoxyethylene radicals to this hydrophobic portion tends to increase the water-solubility of the molecule as a whole and the liquid character of the products is retained up to the point where polyoxyethylene content is about 50% of the total weight of the condensation product.

Other suitable nonionic surfactants include, for example:

(i) The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 5 to about 25 moles of ethylene oxide per mole of alkyl phenol. The alkyl substituent in such compounds may be derived from polymerized propylene, diisobutylene, octane, and nonane, for example. Examples of compounds of this type include nonyl phenol condensed with about 9.5 moles of ethylene oxide per mole of phenol; dodecyl phenol condensed with about 12 moles of ethylene oxide per mole of phenol; dinonyl phenol condensed with about 15 moles of ethylene oxide per mole of phenol; and diisooctyl phenol condensed with about 15 moles of ethylene oxide per mole of phenol. Commercially available nonionic surfactants of this type include Igepal CO-630, marketed by the GAF Corporation; and Triton X-45, X-114, X-100, and X-102, all marketed by the Rohm & Haas Company.

(ii) Those derived from the condensation of ethylene oxide with the product resulting from the reaction of propylene oxide and ethylene diamine-products which may be varied in composition depending upon the balance between the hydrophobic and hydrophilic elements which is desired. Examples are compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2500 to 3000. Examples of this type of nonionic surfactant include certain of the commercially available Tetronic compounds, marketed by Wyandotte Chemical Corporation.

(iii) The condensation product of aliphatic alcohols having from 8 to 18 carbon atoms, in either straight or branched chain configuration, with ethylene oxide, e.g., a coconut alcohol ethylene oxide condensate having from 10 to 30 moles of ethylene oxide per mole of coconut alcohol. Examples of commercially available nonionic surfactants of this type include Tergitol 15-S-9 (the condensation product of $C_{11}$–$C_{15}$ secondary alcohol with 9 moles ethylene oxide), marketed by Union Carbide Corporation; Neodol 45-9 (the condensation product of $C_{14}$–$C_{15}$ linear alcohol with 9 moles of ethylene oxide), Neodol 45-7 (the condensation product of $C_{14}$–$C_{15}$ linear alcohol with 7 moles of ethylene oxide), Neodol 45-4 (the condensation product of $C_{14}$–$C_{15}$ linear alcohol with 4 moles of ethylene oxide), marketed by Shell Chemical Company, and Kyro EOB (the condensation product of $C_{13}$–$C_{15}$ linear alcohol with 9 moles of ethylene oxide), marketed by The Procter & Gamble Company.

(iv) Trialkyl amine oxides and trialkyl phosphine oxides wherein one alkyl group ranges from 10 to 18 carbon atoms and two alkyl groups range from 1 to 3 carbon atoms; the alkyl groups can contain hydroxy substituents. Specific examples include dodecyl (di-2-hydroxyethyl)amine oxide and tetradecyl dimethyl phosphine oxide.

Zwitterionic surfactants comprise the betaine and betaine-like compounds wherein the molecule contains both basic and acidic groups which form an inner salt giving the molecule both cationic and anionic hydrophilic groups over a broad range of pH values.

Some common examples of these surfactants are described in U.S. Pat. Nos. 2,082,275, 2,702,279 and 2,555,082, incorporated herein by reference. Suitable zwitterionic surfactants have the formula

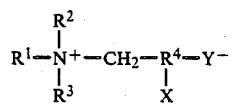

wherein $R^1$ is an alkyl radicla containing from about 8 to about 22 carbon atoms, $R^2$ and $R^3$ contain from about 1 to about 3 carbon atoms, $R^4$ is an alkylene chain containing from about 1 to about 4 carbon atoms, X is selected from the group consisting of hydrogen and a hydroxyl radical, Y is selected from the group consisting of carboxyl and sulfonyl radicals and wherein the sum of the $R^1$, $R^2$ and $R^3$ radicals is from about 14 to about 26 carbon atoms.

Amphoteric and ampholytic surfactants which can be either cationic or anionic depending upon the pH of the system are represented by detergents such as dodecyl-beta-alanine, N-alkyltaurines such as the one prepared by reacting dodceylamine with sodium isethionate according to the teaching of U.S. Pat. No. 2,658,072, N-higher alkylaspartic acids such as those produced according to the teaching of U.S. Pat. No. 2,438,091, and the products sold under the trade name "Miranol" and described in U.S. Pat. No. 2,528,378, said patents being incorporated herein by reference.

Additional surfactants useful in the present invention can be found in McCutcheon's *Detergents and Emulsifiers*, North American Ed. pages 317–324 (1986), incorporated herein by reference.

The cleaning compositions of the present invention can optionally contain, at their art-established levels, materials which are conventionally used in skin cleansing compositions.

Conventional antibacterial agents and sanitizers can be included in the skin cleansing compositions at levels of from about 0.5% to about 4%. Typical antibacterial sanitizers which are suitable for use herein include 3,4-di- and 3,4',5'-bromosalicylanilides; 4,4'-dichloro-3-(trifluoromethyl)carbanilide; 3,4,4'-trichlorocarbanilide and mixtures of these materials. Use of these and related materials in skin cleansing compositions is described in more detail in Reller, et al., U.S. Pat. No. 3,256,200, issued June 14, 1966, incorporated herein by reference.

Nonionic emollients can be included as skin conditioning agents in the skin cleansing compositions of the present invention at levels up to about 10%. Such materials include for example, mineral oils, paraffin wax having a melting point of from about 100° F. to about 170° F., fatty sorbitan esters (see U.S. Pat. No. 3,988,255, Seiden, issued Oct. 26, 1976, incorporated by reference herein), lanolin and lanolin derivatives, esters such as isopropyl myristate and triglycerides such as coconut oil or hydrogenated tallow.

Free fatty acid, such as coconut oil fatty acid, can be added to the compositions herein at levels up to about 10% to improve the volume and quality (creaminess) of the lather produced by the compositions.

Perfumes, dyes and pigments can also be incorporated into the skin cleansing compositions of the invention. Perfumes are preferably used at levels of from about 0.5% to 3%, and dyes and pigments are preferably used at levels of from about 0.001% to about 0.5%.

A particularly preferred optional ingredient is a cationic or nonionic polymeric skin feel aid. Reduced skin irritation benefits of both types of polymers are set out in "Polymer JR for Skin Care" Bulletin, by Union Carbide, 1977. The cationics are preferred over the nonionics, for use herein, because they provide better skin feel benefits. Examples of the cationic polymers and the nonionic polymers useful for this purpose are set out below.

The amount of polymeric skin feel aid found useful in the present invention is from about 0.5% to about 5%, preferably from about 0.1% to about 2%, and more preferably from about 0.1% to about 1%, of the composition.

A particularly preferred skin feel aid is cationic (quaternized) guar gum, e.g., Jaguar C-14-S, from Celanese Corp.

Other types of high molecular weight polymeric skin feel agents useful herein include nonionic guar gums, Merquats 100 and 550, made by Merck & Co., Inc.; UCARE polymer JR-400, made by Union Carbide Corp.; Mirapol A15 made by Miranol Chemical Company, Inc.; and Galactasol 811, made by Henkel, Inc.

The nonionic polymers found to be useful as skin feel aids include the nonionic polysaccharides, e.g., nonionic hydroxypropyl guar gums, sold by Celanese Water Soluble Polymers, a Division of Celanese Corp. A preferred nonionic hydroxypropyl guar gum material is Jaguar$^R$ HP-60 having hydroxypropyl molar substitution of about 0.6. Another class of useful nonionic skin feel aids include cellulosic nonionic polymers, e.g., hydroxyethylcellulose and carboxymethylcellulose.

In addition to the aforementioned components, optional humectants, thickening agents, preservatives, alkaline agents, the skin conditioning propoxylated glycerol derivatives, or cosmetic adjuvants may also be used in the skin cleansing compositions.

Skin cleansing compositions formulated as toilet soap bars generally comprise from about 50% to about 90% surfactant. Moisture is generally present at levels of from about 5% to about 20%. Skin cleansing compositions formulated as liquids generally comprise from about 10% to about 30% surfactant and from about 60% to about 90% water. Skin cleansing compositions formulated as pastes generally comprise from about 20% to about 60% surfactant and from about 30% to about 50% water. Pastes and liquids will also generally contain organic thickening agents such as natural gums and polymers.

Examples of soap-based toilet bar compositions are found in U.S. Pat. No. 3,567,749, Megson et al., issued Apr. 27, 1971, incorporated herein by reference. Examples of synthetic-based toilet bars which can be used in preparing compositions of the present invention are found in U.S. Pat. No. 2,987,484, Lundberg et al., issued June 6, 1961, incorporated by reference herein. Other examples of soap/synthetic-based toilet bars are found in U.S. Pat. No. 3,070,547, Chaffee, issued Dec. 25, 1962 and U.S. Pat. No. 3,376,229, Haas et al., issued Apr. 2, 1968, incorporated herein by reference. Examples of soap-based liquid cleansing compositions which can be used in preparing liquid compositions of the present invention are found in U.S. Pat. No. 4,310,433, Stiros, issued Jan. 12, 1982, incorporated herein by reference. Examples of synthetic-based liquid cleansing compositions which can be used in preparing compositions of the present invention are found in U.S. Pat. No. 4,338,211, Stiros, issued June 6, 1982, incorporated herein by reference. Paste compositions can be made by appropriate reduction in the levels of water in the compositions of U.S. Pat. Nos. 4,310,433 and 4,338,211.

The skin cleansing compositions of this invention can also be formulated into a pressurized aerosol mousse composition. The mousse composition contains from about 88% to about 97%, preferably from about 90% to about 96%, of a solution type of formulation (that has been concentrated), and from about 3% to about 12%, preferably from about 4% to about 10%, of a propellant. Preferred surfactants useful in these compositions are described in European Patent Application No. 0194097, Schmidit et al., published Sept. 10, 1986, incorporated herein by reference. A particularly preferred propellant is a mixture of butane, isobutane, and propane, known commercially as Propellant A46, made by Phillips Chemical Company, a subsidiary of Phillips Petroleum Company.

The skin cleansing compositions of the present invention preferably also comprise a substantivity agent to prevent wash-off and to assure deposition of the tocopherol sorbate onto the skin. Suitable substantivity agents are guar gum and Polymer JR.

Combination Actives

Sunscreens

Optimum protection against sun damage can be obtained by using a combination of the non-sunscreening photoprotection agent of the present invention together with sunscreens. The photoprotecting capability of tocopherol sorbate is primarily against UVB radiation. Thus, the combination of tocopherol sorbate with a UVA sunscreen would be most desirable. Additional UVB protection may also be included in such compositions. The inclusion of sunscreens in compositions of the present invention at low levels will not significantly reduce the tanning response of the user but will enhance immediate protection against acute UV damage.

A wide variety of conventional sunscreening agents are suitable for use in combination with tocopherol sorbate. Segarin, et al., at Chapter VIII, Pages 189 et seq., of *Cosmetics Science and Technology*, disclose numerous suitable agents. Specific suitable sunscreening agents include, for example: p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropyleneglycol esters); Cinnamic acid derivatives (menthyl and benzyl esters, α-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane.

Of these, 2-ethylhexyl p-methoxycinnamate, 4,4'-t-butyl methoxydibenzoylmethane, 2-hydroxy-4-methoxybenzophenone, octyl dimethyl p-aminobenzoic acid, digalloyltrioleate, 2,2-dihydroxy-4-methoxybenzophenone, ethyl 4-[bis(hydroxypropyl)]aminobenzoate, 2-ethylhexyl 2-cyano-3,3-diphenylacrylate, 2-ethylhexyl salicylate, glyceryl p-aminobenzoate, 3,3,5-trimethylcyclohexyl salicylate, methyl anthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfonic benzoxazoic acid and mixtures of these compounds, are particularly useful.

Preferred sunscreens useful in the compositions of the present invention are 2-ethylhexyl p-methoxycinnamate, butyl methoxydibenzoylmethane, 2-hydroxy-4-methoxybenzophenone, octyl dimethyl p-aminobenzoic acid and mixtures thereof.

A safe and photoprotectively effective amount of sunscreen may be used in the tocopherol sorbate compositions of the present invention. By "safe and photoprotective" is meant an amount sufficient to provide photoprotection when the composition is applied but not so much as to cause any side effects or skin reactions. The sunscreening agent must also be compatible with the tocopherol sorbate. By "compatible" is meant that the sunscreening agent must be capable of being commingled with tocopherol sorbate in a manner such that there is no interaction which would substantially reduce the efficacy of the composition for photoprotection. Generally from about 1% to about 20%, preferably from about 2% to about 10%, of the composition may comprise a sunscreening agent. Exact amounts will vary depending upon the sunscreen chosen and the desired Sun Protection Factor (SPF).

SPF is a commonly used measure of photoprotection of a sunscreen against erythema. This number is derived from another parameter, the minimal erythemal dose (MED). MED is defined as the "least exposure dose at a specified wavelength that will elicit a delayed erythema response." The MED indicates the amount of energy reaching the skin and the responsivenes of the skin to the radiation. The SPF of a particular photoprotector is obtained by dividing the MED of protected skin by the MED of unprotected skin. The higher the SPF, the more effective the agent in preventing sunburn. The SPF value tells how many times longer a person can stay in the sun with use of the sunscreen (compared to a person with unprotected skin) before that person will experience 1 MED. For example, utilizing a sunscreen with an SPF of 6 will allow an individual to stay in the sun six times longer before receiving 1 MED. As the SPF value of a sunscreen increases, the less chance exists for development of tanning of the skin. Commercially available sunscreening products have SPF values ranging from 2 to 34.

Tocopherol sorbate's photoprotecting capability against erythema can also be measured. Tocopherol sorbate provides erythema reduction equivalent to an SPF-2 sunscreen. When an SPF-2 sunscreen agent is utilized with tocopherol sorbate for protection against sunburn, the combination provides protection equivalent to an SPF-4 sunscreen.

It is much more difficult to measure the benefits achieved by the use of tocopherol sorbate against long-term effects of UV exposure, such as premature aging of the skin. One method for measuring photo-induced wrinkling of skin is disclosed in "An Animal Model of Solar-Aged Skin: Histological, Physical, and Visible Changes in UV-Irradiated Hairless Mouse Skin", Bissett et al., *Photochem. Photobiol.*, 46 pp. 367-378 (1987).

Also particularly useful in the present invention are sunscreens such as those disclosed in Sabatelli, U.S. patent application Ser. No. 054,085 (filed June 2, 1987) and Sabatelli et al., U.S. patent application Ser. No. 054,046 (filed June 2, 1987). The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

These sunscreening agents provide higher efficacy, broader UV absorption, lower skin penetration and longer lasting efficacy relative to conventional sunscreens.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl)methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl)methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone; and N,N-di-(2-ethylhexyl)-4-aminobenzoic acid ester of 4-(2-hydroxyethoxy)dibenzoylmethane and mixtures thereof.

The compositions of the present invention, with or without sunscreens may also be formulated as shampoos, conditioners, mousses or other hair care products. It is known that UV radiation damages hair and the photoprotecting agents of the present invention may minimize such damage. Furthermore such formulations will provide a means for applying the photoprotecting agents of the present invention onto the scalp, which is also susceptible to UV damage. Any compatible art-recognized hair care formulations can be used with tocopherol sorbate added at a level of from about 1% to about 5%. If desired, a sunscreen may also be included at from about 1% to about 5%.

An agent may also be added to any of the compositions of the present invention to improve the skin substantivity of those compositions, particularly to enhance their resistance to being washed off by water, or rubbed off. A preferred agent which will provide this benefit is a copolymer of ethylene and acrylic acid. Compositions comprising this copolymer are disclosed in U.S. Pat. No. 4,663,157, Brock, issued May 5, 1987, which is incorporated herein by reference. The disclosed skin substantivity agent comprises the polymeric form of two monomers, ethylene and acrylic acid, to yield the following:

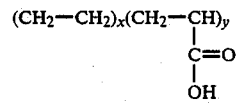

wherein the ratio of x:y is from about 1:24 to about 1:9, and wherein the weight average molecular weight of the molecule is from about 3500 to about 4500, preferably from about 4000 to about 4300. These copolymers are preferably included in an oil-in-water emulsion sunscreen composition comprising: (a) from about 1% to about 20% of tocopherol sorbate plus an optional oil-soluble sunscreen; (b) from about 0.25% to about 3% of the ethylene-acrylic acid copolymer as described above; (c) from about 2% to about 10% of an emulsifier; and (d) from about 70% to about 90% of water wherein the ratio of photoprotecting agents to the copolymer is from about 12:1 to about 15:1. Sunscreening agents which are particularly useful in combination with these copolymers are 2-ethylhexyl p-methoxycinnamate, butyl methoxydibenzoylmethane, 2-hydroxy-4-methoxybenzophenone, octyldimethyl p-aminobenzoic acid and mixtures thereof.

Anti-Inflammatory Agents

In a preferred photoprotection composition of the present invention, an anti-inflammatory agent is included as an active along with tocopherol sorbate. The inclusion of an anti-inflammatory agent enhances the photoprotection benefits of the compositions. The anti-inflammatory agent protects strongly in the UVA radiation range (though it may provide some UVB protection as well), while tocopherol sorbate protects strongly in the UVB radiation range. Thus the combination provides broad protection. The topical use of anti-inflammatory agents to reduce the effects of *acute* exposure, i.e., erythema, to UV radiation is known. However, it has now been discovered that the chronic use of anti-inflammatories also greatly reduces photo-aging of the skin resulting from *chronic* exposure to UV radiation. It has also been discovered that the combination of an anti-inflammatory agent and tocopherol sorbate provides greater photoprotection than is provided by each active alone. Furthermore, the combination provides greater photoprotection than is provided by the sum of the effects of each active alone. By greater photoprotection is meant both reduction of acute effects of UV exposure, e.g., erythema and reduction of chronic effects of UV exposure, e.g., premature wrinkling and sagging of the skin.

A safe and photoprotectively effective amount of an anti-inflammatory agent may be added to the compositions of the present invention. By "safe and photoprotectively effective" amount is meant an amount sufficient to provide photoprotection when the composition is properly applied, but not so much as to cause any side effects or adverse skin reactions; generally from about 0.1% to about 10%, preferably from about 0.5% to about 5%, of the composition. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone, hydroxyltriamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof may be used. The preferred steroidal anti-inflammatory for use in the present invention is hydrocortisone.

A second class of anti-inflammatory agents which is useful in the compositions of the present invention includes the non-steroidal anti-inflammatory agents. The variety of compounds encompassed by this group are well-known to those skilled in the art. For detailed disclosure of the chemical structure, synthesis, side effects, etc., of non-steroidal anti-inflammatory agents, reference may be had to standard texts, including *Anti-Inflammatory and Anti-Rheumatic Drugs*, K. D. Rainsford, Vol. I–III, CRC Press, Boca Raton, (1985), and *Anti-inflammatory Agents, Chemistry and Pharmacology*, 1, R. A. Scherrer, et al., Academic Press, New York (1974), incorporated herein by reference.

Specific non-steroidal anti-inflammatory agents useful in the composition of the present invention include, but are not limited to:

(1) the oxicams, such as piroxicam, isoxicam, tenoxicam, sudoxicam, and CP-14,304;

(2) the salicylates, such as aspirin, disalcid, benorylate, trilisate, safapryn, solprin, diflunisal, and fendosal;

(3) the acetic acid derivatives, such as diclofenac, fenclofenac, indomethacin, sulindac, tolmetin, isoxepac, furofenac, tiopinac, zidometacin, acemetacin, fentiazac, zomepirac, clidanac, oxepinac, and felbinac;

(4) the fenamates, such as mefenamic, meclofenamic, flufenamic, niflumic, and tolfenamic acids;

(5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and (6) the pyrazoles, such as phenylbutazone, oxyphenbutazone, feprazone, azapropazone, and trimethazone.

Mixtures of these non-steroidal anti-inflammatory agents may also be employed, as well as the pharmaceutically-acceptable salts and esters of these agents. For example, etofenamate, a flufenamic acid derivative, is particularly useful for topical use. Of the nonsteroidal anti-inflammatory agents, ibuprofen, naproxen, flufenamic acid, mefenamic acid, meclofenamic acid, piroxicam and felbinac are preferred, and ibuprofen, naproxen, and flufenamic acid are most preferred.

Another class of anti-inflammatory agents which are useful in the present invention are the anti-inflammatory agents disclosed in U.S. patent application Ser. No. 879,863, Loomans et al., filed June 27, 1986. This application discloses a class of non-steroidal anti-inflammatory compounds which comprise specifically-substituted phenyl compounds, especially substituted 2,6-di-tert-butyl phenol derivatives. For example, compounds selected from 4-(4'-pentyn-3'-one)-2,6-di-t-butylphenol; 4-(5'-hexynoyl)-2,6-di-t-butylphenol; 4-((S)-(−)-3'-methyl-5'-hexynoyl)-2,6-di-t-butylphenol; 4-((R)-(+)-(3'-methyl-5'-hexynoyl)-2,6-di-t-butylphenol; and 4-(3',3'-dimethoxy propionyl)-2,6-di-t-butylphenol are useful in the present invention.

Yet another class of anti-inflammatory agents which are useful in the present invention are those disclosed in U.S. Ser. No. 051,446, Mueller, filed May 18, 1987. This application discloses compounds and diastereomeric mixtures of specific 2-naphthyl-containing ester compounds, especially naproxen ester and naproxol ester compounds, having two or more chiral centers. For example, compounds selected from (S)-naproxen-(S)-2-butyl ester, (S)-naproxen-(R)-2-butylester, (S)-naproxol-(R)-2-methyl butyrate, (S)-naproxol-(S)-2-methyl butyrate, diasteromeric mixtures of (S)-naproxen-(S)-2-butyl ester and (S)-naproxen-(R)-2-butyl ester, and diasteromeric mixtures of (S)-naproxol-(R)-2-methyl butyrate and (S)-naproxol-(S)-2-methyl butyrate are useful in the present invention.

Finally, so-called "natural" anti-inflammatory agents are useful in the present invention. For example, candelilla wax, alpha-bisabolol, aloe vera, Manjistha (extracted from plants in the genus Rubia, particularly *Rubia cordifolia*), and Guggal (extracted from plants in the genus Commiphora, particularly *Commiphora mukul*), may be used.

An even more preferred composition of the present inventin comprises tocopherol sorbate, a sunscreen, and an anti-inflammatory agent together for photoprotection. Such a composition comprises about 1% to about 10%, preferably from about 2% to about 5% tocopherol sorbate, from about 1% to about 15%, preferably from about 2% to about 10% of a sunscreen, and from about 0.2% to about 5%, preferably from about 0.5% to about 2% of an anti-inflammatory agent. This combination gives protection broader than that provided with each photoprotector alone. Furthermore, the combination provides greater photoprotection than is provided by the sum of the effects of each active alone. By greater photoprotection is meant both reduction of acute effects of UV exposure, e.g., erythema, and reduction of chronic effects of UV exposure, e.g., premature wrinkling and sagging of the skin.

In the compositions of the present invention other radical scavenging compounds may be used in combination with tocopherol sorbate. For example, ascorbic acid (Vitamin C) and its salts, tocopherol (Vitamin E), other tocopherol esters, butylated hydroxy benzoic acids and their salts, 6-hydroxy-2,5,7,8-tetramethyl-chroman-2-carboxylic acid (commercially available under the tradename Trolox®), gallic acid and its alkyl esters, especially propyl gallate, uric acid and its salts and alkyl esters, sorbic acid and its salts, the ascorbyl esters of fatty acids, amines (e.g., N,N-diethylhydroxylamine, aminoguanidine), sulfhydryl compounds (e.g., glutathione) and dihydroxyfumaric acid and its salts. Each of these compounds has photoprotecting capabilities. However, the use of tocopherol sorbate alone in the present invention is preferred.

From about 1% to about 5% of these radical scavenging compounds may be used in the present invention in combination with the levels of tocopherol sorbate taught herein. Exact amounts will vary depending on which particular compound is used as these compounds vary somewhat in potency.

Method For Preventing Deleterious Effects Caused By UV Exposure

The present invention further relates to a method for protecting the skin of humans and lower animals from the deleterious effects of UV radiation. Such protection by tocopherol sorbate extends not only to damage resulting from acute UV exposure, e.g. erythema, but also to damage resulting from chronic UV exposure, e.g. photoaging.

Such a method comprises applying to the skin of the human or lower animal a safe and photoprotectively effective amount of tocopherol sorbate. This may be accomplished by using a composition comprising tocopherol sorbate as described in the present application. The term "safe and photoprotectively effective amount", as used herein, means an amount sufficient to substantially reduce the deleterious effects of UV-radiation to skin but not so much as to cause any side effects or adverse skin reactions. Typically a safe and photoprotectively effective amount is from about 0.01 mg to about 1.0 mg, preferably from about 0.05 mg to about 0.5 mg, tocopherol sorbate per $cm^2$ skin. The tocopherol sorbate may be simply spread or sprayed onto the skin or may preferably be rubbed into the skin to enhance penetration. The tocopherol sorbate works best if applied prior to or concomitantly with UV exposure. It may also be applied up to about 30 minutes after UV exposure. However, unlike typical sunscreens, which must remain as a coating on the skin throughout UV exposure, the application of tocopherol sorbate may be done up to four hours prior to exposure. This is because the active agent penetrates the skin to work and thus is not as susceptible to rub-off, wash-off or wear-off. For protection against acute damage from UV-radiation, application of tocopherol sorbate just prior to exposure is preferred. For protection against chronic damage from UV-radiation, application of tocopherol sorbate several times daily; generally from about 2 times to about 5 times, preferably 2 times daily, is preferred.

A preferred method of the present invention for preventing deleterious effects caused by UV exposure involves applying both a safe and photoprotectively effective amount of tocopherol sorbate and a safe and photoprotectively effective amount of a sunscreening agent to the skin simultaneously. By simultaneous application is meant applying the agents to the skin at the same situs on the body at about the same time. Though this can be accomplished by applying one of these agents to the skin after application of the other, preferably a composition comprising both agents commingled is applied to the skin. By "safe and photoprotectively effective amount" of sunscreening agent is meant an amount sufficient to substantially reduce the deleterious effects of UV-radiation to skin but not so much as to cause any side effects or adverse skin reactions; generally from about 0.01 mg to about 1.0 mg, preferably from about 0.05 mg to about 0.5 mg, of sunscreening agent per $cm^2$ of skin.

Preferably, the sunscreening agent used in the present method is selected from the group consisting of 2-ethylhexyl p-methoxycinnamate; butyl methoxydibenzoylmethane; 2-hydroxy-4-methoxybenzophenone; octyldimethyl p-aminobenzoic acid; the 4-N,N-(2-ethylhexyl)methylaminobenzoic acid ester of 2,4-dihydroxybenzophenone; the N,N-di-(2-ethylhexyl)-4-aminobenzoic acid ester of 4-hydroxydibenzoylmethane, the 4-N,N-(2-ethylhexyl)methylaminobenzoic acid ester of 4-hydroxy dibenzoylmethane; the 4-N,N-(2-ethylhexyl)methylaminobenzoic acid ester of 2-hydroxy-4-(2-hydroxyethoxy)benzophenone; the 4-N,N-(2-ethylhexyl)methylaminobenzoic acid ester of 4-(2-hydroxyethoxy)dibenzoylmethane; the N-N-di-(2-ethylhexyl)-4-amino benzoic acid ester of 2-hydroxy-4-(2-hydroxyethoxy)benzophenone; the N,N-di-(2-ethylhexyl)-4-amino benzoic acid ester of 4-(2-hydroxyethoxy)dibenzoyl methane, and mixtures thereof.

The tocopherol sorbate and sunscreening agent may be simply spread over the skin, or rubbed into the skin to enhance penetration of the tocopherol sorbate. The active are applied in conjunction with UV exposure, i.e., prior to, during or after UV exposure. For protection against acute damage from UV-radiation, application of the actives just prior to exposure is sufficient. For protection against chronic damage from UV-radiation, application several times daily, e.g., about 2 times daily, is preferred.

The use of anti-inflammatory agents for inhibiting adverse acute effects of UV exposure, e.g., erythema, is known. However, it has now been discovered that anti-inflammatory agents may be used to inhibit adverse chronic effects of UV exposure, e.g., premature wrinkling and sagging of the skin. Thus, the present invention relates to a method for protecting the skin from chronic effects of UV exposure comprising chronic application to the skin of a safe and photoprotectively effective amount of an anti-inflammatory agent. The term "safe and photoprotectively effective amount" as used herein, means an amount sufficient to substantially reduce the deleterious effects of UV-radiation to the skin but not so much as to cause any side effects or adverse skin reactions. Typically a safe and photoprotectively effective amount is from about 0.005 mg to about 0.5 mg, preferably from about 0.01 mg to about 0.1 mg, anti-inflammatory agent per $cm^2$ skin. By "chronic application" is meant application to the skin several times daily, generally from about 2 times to about 5 times, preferably 2 times daily, for an extended period of time greater than seven, preferably greater than 10, days. Preferably this regimen of application is continued for as long as the user chronically exposes him or herself to damaging UV radiation. This may comprise application over a period of several days, months or longer. The anti-inflammatory agent may be simply spread over the skin or may preferably be rubbed into the skin to enhance penetration.

Preferably the anti-inflammatory agent used in the present method is selected from the group consisting of hydrocortisone, ibuprofen, naproxen, flufenamic acid, mefenamic acid, meclofenamic acid, piroxicam, felbinac, 4-(4'-pentyn-3'-one)-2,6-di-t-butylphenol; 4-(5'-hexynoyl)-2,6-di-t-butylphenol, 4-((S)-(—)-3'-methyl-5'-hexynoyl)-2,6-di-t-butylphenol, 4-((R)-(+)-3'-methyl-5'-hexynoyl)-2,6-di-t-butylphenol, 4-(3',3'-dimethoxy propionyl)-2,6-di-t-butylphenol, Manjistha, Guggal, and mixtures thereof.

A more preferred method of the present invention for preventing deleterious effects caused by UV exposure involves applying both a safe and photoprotectively effective amount of tocopherol sorbate and safe and photoprotectively effective amount of an anti-inflammatory agent to the skin simultaneously. By "simultaneously" is meant application of the agents to the skin at the same situs on the body at about the same time. Though this can be accomplished by applying one of these agents to the skin after application of the other, preferably a composition comprising both agents commingled is applied to the skin. By "safe and photoprotectively effective amount" of each agent is meant an amount sufficient to substantially reduce the deleterious effects of UV-radiation to skin but not so much as to cause any side effects or adverse skin reactions; generally from about 0.005 mg to about 0.5 mg, preferably from about 0.01 mg to about 0.1 mg, anti-inflammatory agent per $cm^2$ skin, and from about 0.01 mg to about 1.0 mg, preferably from about 0.05 mg to about 0.5 mg, tocopherol sorbate per $cm^2$ skin. The tocopherol sorbate and anti-inflammatory agent may be simply spread over the skin or may preferably be rubbed into the skin to enhance penetration.

Unlike with tocopherol sorbate alone, the combination of tocopherol sorbate plus anti-inflammatory agent are applied in conjunction with UV exposure, i.e., prior to, concomitantly with, or after UV exposure. More specifically, the combination may be applied up to about 4 hours prior to UV exposure, up to about 30 minutes after UV exposure, or any time in between. This is because the anti-inflammatory agent works to minimize adverse reactions in the skin even if applied after UV exposure. For protection against acute damage from UV-radiation, application of tocopherol sorbate and the anti-inflammatory agent just prior to exposure, or immediately following exposure, is sufficient. For protection against chronic damage from UV-radiation, application of tocopherol sorbate and the anti-inflammatory agent several times daily, e.g., from about 2 times to about 5 times, preferably 2 times daily is preferred.

Yet another method of the present invention for preventing deleterious effects caused by UV exposure involves applying a safe and photoprotectively effective amount of tocopherol sorbate, a safe and photoprotectively effective amount of an anti-inflammatory agent, and a safe and photoprotectively effective amount of sunscreening agent to the skin simultaneously. By "simultaneously" is meant application of the agents to the skin at the same situs on the body at about the same time. Though this can be accomplished by applying the agents to the skin sequentially (one after the other), preferably a composition comprising all three agents commingled is applied to the skin. By "safe and photoprotectively effective amount" of each agent is meant an amount sufficient to substantially reduce the deleterious effects of UV-radiation to skin but not so much as to cause any side effects or adverse skin reactions; generally from about 0.01 mg to about 1 mg, preferably from about 0.05 mg to about 0.5 mg tocopherol sorbate per $cm^2$ skin, from about 0.005 mg to about 0.5 mg, preferably from about 0.01 mg to about 0.1 mg anti-inflammatory agent per $cm^2$ skin, and from about 0.01 mg to about 1 mg, preferably from about 0.05 mg to about 0.5 mg sunscreening agent per $cm^2$ skin. The tocopherol sorbate, anti-inflammatory agent, and sunscreening agent may be simply spread over the skin or may preferably be rubbed into the skin to enhance penetration. The combination is applied in conjunction with UV exposure, i.e., prior to, concomitantly with, or after UV exposure. More specifically, the combination may be applied up to about 4 hours prior to UV exposure, up to about 30 minutes after UV exposure, or any time in between.

For protection against acute damage from UV-radiation, application of tocopherol sorbate, the anti-inflammatory agent, and the sunscreening agent just prior to UV exposure is sufficient. For protection against chronic damage from UV-radiation, application of tocopherol sorbate, the anti-inflammatory agent, and the sunscreening agent several times daily, e.g., from about 2 times to about 5 times, preferably 2 times daily is preferred.

The following examples further describe and demonstrate the preferred embodiments within the scope of the present invention. The examples are given solely for the purpose of illustration, and are not to be construed as limitations of the present invention since many variations thereof are possible without departing from its spirit and scope.

All percentages and ratios herein are by weight, unless otherwise specified.

EXAMPLE I

A moisturizing lotion is prepared by combining the following components utilizing conventional mixing techniques.

| Components | Percent by Weight of Composition |
| --- | --- |
| Water (purified) | 70.94 |
| Carbomer viscosity control agents (commercially available in the Acritamer series from R.I.T.A. Corp.) | 0.23 |
| Alkyl Parabens | 0.90 |
| Glycerin | 3.50 |
| Potassium Hydroxide | 0.09–0.15 |
| Tetrasodium EDTA | 0.10 |
| Cetyl Alcohol | 1.25 |
| Stearic Acid | 0.75 |
| Glyceryl Stearate | 0.63 |
| Polyoxyethylene Stearyl Alcohol (commercially available in the Brij series from ICI Americas, Inc.) | 1.75 |
| Coco-Caprylate/caprate | 2.00 |
| $C_{12}$-$C_{15}$ Alcohol Benzoate (Finsolv TN- commercially available from Finetex, Inc.) | 2.00 |
| Tocopherol Sorbate | 2.00 |
| Octyl Methoxycinnamate | 7.50 |
| Benzophenone-3 | 1.00 |
| Octyl Dimethyl PABA | 1.00 |
| Dimethicone | 0.30 |
| Imidazolidinyl Urea | 0.10 |
| Ethylene Acrylate Copolymer | 3.80 |
| Tyrosine | 0.10 |

This lotion may be topically applied to inhibit damage caused by acute or chronic UV exposure. Use of an amount of lotion sufficient to deposit about 0.5 mg/cm$^2$ of tocopherol sorbate, and about 0.5 mg/cm$^2$ of the sunscreening agents to the skin immediately prior to UV exposure is appropriate. Substantially similar results are obtained if the lotion is applied to the skin up to 4 hours prior to UV exposure or up to 30 minutes after UV exposure.

Substantially similar results are obtained if the octyl methoxycinnamate, benzophenone-3, and octyl dimethyl PABA are replaced, in whole or in part, with 2-ethylhexyl p-methoxycinnamate, butyl methoxydibenzoylmethane, 2-hydroxy-4-methoxybenzophenone, and mixtures thereof.

EXAMPLE II

A skin lotion is prepared by combining the following components utilizing conventional mixing techniques.

| Component | Percent by Weight Of Composition |
| --- | --- |
| 4-N,N—(2-Ethylhexyl)methylamino Benzoic Acid Ester of 4-(2-Hydroxyethoxy)-Dibenzoyl Methane | 10.00 |
| Water(purified) | 47.54 |
| Dimethyl Isosorbide | 8.00 |
| Dioctyl Maleate | 8.00 |
| $C_{12-15}$ Alcohol Benzoate (Finsolv TN-commercially available from Finetex, Inc.) | 8.00 |
| Glycerin | 3.50 |
| Ethylene Acrylate Copolymer | 3.80 |
| Tocopherol Sorbate | 2.00 |
| Cetyl Alcohol | 1.75 |
| Polyoxyethylene Stearyl Alcohol (commercially available in the Brij series from ICI Americas, Inc.) | 1.75 |
| Stearic Acid | 1.25 |
| Glyceryl Stearate | 1.13 |
| Alkyl Parabens | 0.90 |
| Titanium Dioxide | 0.40 |
| Dimethicone | 0.30 |
| Carbomer viscosity control agents (commercially available in the Acritamer series from R.I.T.A. Corp.) | 0.23 |
| Imidazolidinyl Urea | 0.10 |
| Potassium Hydroxide | 0.15 |
| Tyrosine | 0.10 |
| Tetrasodium EDTA | 0.10 |

This lotion is useful for topical application to inhibit damage caused by acute or chronic UV exposure. Use of an amount of lotion sufficient to deposit about 0.5 mg/cm$^2$ of tocopherol sorbate and about 0.5 mg/cm$^2$ of the sunscreening agents to the skin immediately prior to UV exposure is appropriate. Substantially similar results are obtained if the lotion is applied to the skin up 4 hours prior to UV exposure or up to 30 minutes after UV exposure.

Substantially similar results are obtained if the 4-N,N-(2-ethylhexyl)methylaminobenzoic acid ester of 4-(2-hydroxyethoxy)dibenzoylmethane is replaced, in whole or in part, with the 4-N,N-(2-ethylhexyl)methylaminobenzoic acid ester of 2,4-dihydroxybenzophenone, the N,N-di-(2-ethylhexyl)-4-aminobenzoic acid ester of 4-hydroxydibenzoylmethane, the 4-N,N-(2-ethylhexyl)methylaminobenzoic acid ester of 2-hydroxy-4-(2-hydroxyethoxy)benzophenone, the 4-N,N-(2-ethylhexyl)methylaminobenzoic acid ester of 4-(2-hydroxyethoxy)dibenzoylmethane, the N-N-di-(2-ethylhexyl)-4-aminobenzoic acid ester of 2-hydroxy-4-(2-hydroxyethoxy)benzophenone, or the N,N-di-(2-ethylhexyl)-4-aminobenzoic acid ester of 4-(2-hydroxyethoxy)dibenzoylmethane, and mixtures thereof.

EXAMPLE III

A suntan cream is prepared by combining the following components utilizing conventional mixing techniques.

| Component | Percent by Weight of Composition |
| --- | --- |
| Mineral Oil | 20.00 |
| Octyl Palmitate | 10.00 |
| Glyceryl Isostearate | 4.00 |
| Octyl Methoxycinnamate | 7.50 |
| Oxybenzone | 3.00 |
| Polyethylene (AC-617-A,AC-6-A available from Allied Chemical) | 2.00 |
| Alkyl parabens | 0.30 |
| Glycerin | 2.00 |
| Tocopherol Sorbate | 2.00 |
| Ibuprofen | 1.00 |
| Water (purified) | q.s. |

This cream is useful for topical application to inhibit damage caused by acute or chronic UV exposure. Use of an amount of cream sufficient to deposit about 0.5 mg/cm² of tocopherol sorbate, about 0.5 mg/cm² of the sunscreening agents, and about 0.1 mg/cm² of ibuprofen to the skin immediately following UV exposure is appropriate. Substantially similar results are obtained if the cream is applied to the skin up to 4 hours prior to UV exposure or up to 30 minutes following UV exposure.

Substantially similar results are obtained if the octyl methoxy cinnamate and the oxybenzone are replaced, in whole or in part, with 2-ethylhexyl p-methoxycinnamate, butyl methoxydibenzoyl methane, 2-hydroxy-4-methoxybenzophenone, and mixtures thereof.

Substantially similar results are obtained if the ibuprofen is replaced, in whole or in part, with hydrocortisone acetate, naproxen, flufenamic acid, mefenamic acid, meclofenamic acid, piroxicam, felbinac, 4-(4'-pentyn-3'-one)-2,6-di-t-butylphenol, 4-(5'-hexynoyl)-2,6-di-t-butylphenol, 4-(S)-(−)-3'-methyl-5'-hexynoyl-2,6-di-t-butylphenol, 4-(R)-(+)-3'-methyl-5'-hexynoyl-2,6-di-t-butylphenol, 4-(3',3'-dimethoxypropionyl)-2,6-di-t-butylphenol, Manjistha, Guggal, and mixtures thereof.

EXAMPLE IV

A suntan stick is prepared by combining the following components utilizing conventional mixing techniques.

| Component | Percent by Weight of Composition |
| --- | --- |
| Candelilla Wax | 19.25 |
| Ozokerite Wax | 19.25 |
| Petrolatum | 19.25 |
| Lanolin | 15.00 |
| Mineral Oil | 14.85 |
| Octyl Dimethyl PABA | 7.00 |
| Benzophenone-3 | 3.00 |
| BHA (preservative: butylated hydroxy anisole) | 0.05 |
| Propylparaben | 0.10 |
| Tocopherol Sorbate | 5.00 |
| Flavor | q.s. |

This stick is useful for topical application, for example to the lips, to inhibit damage caused by acute or chronic UV exposure. Use of an amount of stick sufficient to deposit about 1.0 mg/cm² of tocopherol sorbate, and about 0.5 mg/cm² of the sunscreening agents to the lips immediately prior to UV exposure is appropriate. Substantially similar results are obtained if the stick is applied up to 4 hours prior to UV exposure or up to 30 minutes after UV exposure.

Substantially similar results are obtained if the octyl dimethyl PABA and the benzophenone-3 are replaced, in whole or in part, with 2-ethylhexyl p-methoxycinnamate, butyl methoxydibenzoylmethane, 2-hydroxy-4-methoxybenzophenone, and mixtures thereof.

EXAMPLE V

A low SPF suntan cream is prepared by combining the following components utilizing conventional mixing techniques.

| Component | Percent by Weight of Composition |
| --- | --- |
| Tetrasodium EDTA | 0.05 |
| Alkylparabens | 0.30 |
| Carbopol (polyacrylic acid polymer-commercially available from | 0.20 |

-continued

| Component | Percent by Weight of Composition |
| --- | --- |
| B.F. Goodrich Chemical) | |
| Glycerin | 2.00 |
| Laureth-23 (polyethylene glycol ether of lauryl alcohol) | 3.00 |
| Sorbitan Stearate | 1.50 |
| Octyl Dimethyl PABA | 3.00 |
| Dimethicone | 2.00 |
| Stearyl Alcohol | 6.00 |
| Triethanolamine | 0.20 |
| Tocopherol Sorbate | 2.00 |
| Water (purified) | q.s. |

This cream is useful for topical application to inhibit damage caused by acute or chronic UV exposure. Use of an amount of cream sufficient to deposit about 0.5 mg/cm² of tocopherol sorbate, and about 0.5 mg/cm² of the sunscreening agents to the skin immediately prior to UV exposure is appropriate. Substantially similar results are obtained if the cream is applied to the skin up to 4 hours prior to UV exposure or up to 30 minutes after UV exposure.

Substantially similar results are obtained if the octyl dimethyl PABA is replaced, in whole or in part, with 2-ethylhexyl p-methoxycinnamate, butyl methoxydibenzoylmethane, 2-hydroxy-4-methoxybenzophenone, and mixtures thereof.

EXAMPLE VI

A suntan aqueous face gel is prepared by combining the following components utilizing conventional mixing techniques.

| Component | Percent by Weight Of Composition |
| --- | --- |
| Water (purified) | 50.00 |
| Aloe | 38.00 |
| Carbopol | 1.00 |
| Glycerin | 3.00 |
| Methylparaben | 0.20 |
| Triethanolamine | 0.90 |
| 2-Phenyl-Benzimedoic Sulfonic Acid | 2.00 |
| Octoxynol-13 (ethoxylated alkyl phenol $(C_8H_{17})(C_6H_4)(OCH_2CH_2)_nOH$, n = av. val. 13) | 1.50 |
| Tocopherol Sorbate | 2.00 |
| Color and Fragrance | q.s. |

This aqueous face gel is useful for application to the face to inhibit damage caused by acute or chronic UV exposure. Use of an amount of gel to deposit about 0.5 mg/cm² of tocopherol sorbate to the face immediately prior to UV exposure is appropriate. Substantially similar results are obtained if the gel is applied to the face up to 4 hours prior to UV exposure or up to 30 minutes after UV exposure.

EXAMPLE VII

A suntan gel is prepared by combining the following components utilizing conventional mixing techniques.

| Component | Percent by Weight of Composition |
| --- | --- |
| Ozokerite Wax | 10.00 |
| Paraffin | 10.00 |
| Petrolatum | 10.00 |
| Isopropyl Myristate | 5.00 |

-continued

| Component | Percent by Weight of Composition |
|---|---|
| Mineral Oil | 58.00 |
| Octyl Dimethyl PABA | 2.50 |
| Propylparaben | 0.10 |
| BHA | 0.05 |
| Tocopherol Sorbate | 2.00 |
| Naproxen | 2.00 |
| Fragrance and Color | q.s. |

This suntan gel is useful for topical application to inhibit damage caused by acute or chronic UV exposure. Use of an amount of gel to deposit about 0.5 mg/cm$^2$ of tocopherol sorbate, about 0.5 mg/cm$^2$ of the sunscreening agent, and about 0.1 mg/cm$^2$ of naproxen to the skin immediately following UV exposure is appropriate. Substantially similar results are obtained if the gel is applied to the skin up to 30 minutes after UV exposure or up to 4 hours prior to UV exposure.

Substantially similar results are obtained if the octyl dimethyl PABA is replaced, in whole or in part, with 2-ethylhexyl p-methoxycinnamate, butyl methoxydibenzoylmethane, 2-hydroxy-4-methoxy-benzophenone, and mixtures thereof.

Substantially similar results are obtained if the naproxen is replaced, in whole or in part, with hydrocortisone acetate, ibuprofen, flufenamic acid, mefenamic acid, meclofenamic acid, piroxicam, felbinac, 4-(4'-pentyn-3'-one)-2,6-di-t-butylphenol, 4-(5'-hexynoyl)-2,6-di-t-butylphenol, 4-(S)-(−)-3'-methyl-5'-hexynoyl-2,6-di-t-butylphenol, 4-(R)-(+)-3'-methyl-5'-hexynoyl-2,6-di-t-butylphenol, 4-(3',3'-dimethoxy propionyl)-2,6-di-t-butylphenol, Manjistha, Guggal, and mixtures thereof.

EXAMPLE VIII

A suntan oil is prepared by combining the following components utilizing conventional mixing techniques.

| Component | Percent by Weight of Composition |
|---|---|
| Sesame Oil | 5.0 |
| Cyclomethicone | 20.0 |
| Isopropyl Myristate | 5.0 |
| BHA | 0.05 |
| Sorbitan Oleate | 1.0 |
| Octyl Dimethyl PABA | 1.5 |
| Propylparaben | 0.7 |
| Tocopherol Sorbate | 2.00 |
| Mineral Oil | q.s. |

This suntan oil is useful for topical application to inhibit damage caused by acute or chronic UV exposure. Use of an amount of oil sufficient to deposit about 0.5 mg/cm$^2$ of tocopherol sorbate, and about 0.5 mg/cm$^2$ of the sunscreening agent to the skin immediately prior to UV exposure is appropriate. Substantially similar results are obtained if the oil is applied to the skin up to 4 hours prior to UV exposure or up to 30 minutes after UV exposure.

Substantially similar results are obtained if the octyl dimethyl PABA is replaced, in whole or in part, with 2-ethylhexyl p-methoxycinnamate, butyl methoxydibenzoylmethane, 2-hydroxy-4-methoxybenzophenone, and mixtures thereof.

EXAMPLE IX

A moisturizing oil-in-water-in-silicone sunscreen emulsion lotion is formed from the following ingredients.

| Ingredient | Percent by Weight of Composition |
|---|---|
| Aqueous Phase: | |
| Purified Water | 57.17 |
| Pantethine, 80% aq. soln. (humectant) | 0.10 |
| Methylparaben | 0.20 |
| Carbomer viscosity control agent (commercially available in the Acritamer series from R.I.T.A. Corp.) | 0.10 |
| Glycerin | 2.50 |
| Sodium alkyl polyether sulfonate (anionic emulsifier) | 0.10 |
| Oil Phase: | |
| Heavy mineral oil | 1.75 |
| Cholesterol | 1.00 |
| Cetyl palmitate | 0.20 |
| PEG-22/Dodecyl glycol copolymer | 0.20 |
| Ethylparaben | 0.10 |
| Propylparaben | 0.15 |
| Neutralizer Base: | |
| Triethanolamine | 0.10 |
| Color & Fragrance: | |
| FD&C Red No. 4 (1% aq. soln.) | 0.03 |
| Odorant Oil | 0.30 |
| Silicone Phase: | |
| Cyclomethicone/Dimethicone copolyol (90:10) | 9.50 |
| Cyclomethicone/Dimethiconol (13:87) | 5.00 |
| Cyclomethicone | 3.00 |
| Phenyl Dimethicone | 1.00 |
| Pareth-15-3 (polyethylene glycol ester of a mixed synthetic $C_{11}$-$C_{15}$ fatty alcohol, av = moles EO) | 2.00 |
| Octyl Methoxycinnamate | 7.00 |
| Benzophenone-3 | 0.50 |
| Naproxen | 2.00 |
| Tocopherol Sorbate | 2.00 |
| $C_{12-15}$ Alcohols Benzoate | 2.85 |

In a suitably sized vessel equipped with a suitable mechanical stirrer (Tekmar Model RW-20 stirring motor, manufactured by IKA-WERK, Germany), the water, panthethine, methylparaben, glycerine and sulfonate emulsifier are heated to about 72°–75° C. and mixed. Stirring is increased until a vortex forms in the aqueous solution. The thickener, Carbomer, is slowly added to the vortex and allowed to mix until completely hydrated and the resultant gel solution is free of gelatinous particles and is uniform in composition. The temperature is maintained at about 72°–75° C. with constant agitation.

The oil phase ingredients are added to a separate suitably sized vessel and heated to about 80°–85° C. using slow mechanical stirring once the oil phase becomes molten. At this point the sunscreening agents, naproxen and tocopherol sorbate are mixed in. When molten, agitation is maintained to keep the oil phase uniform during heating.

The heated oil phase is then slowly added to the heated water phase with stirring to form the oil-in-water emulsion. After addition is complete, the mechanical stirring means is slowed to avoid unnecessary aeration of the emulsion and mixing is continued for approximately fifteen minutes at 70°–75° C. The emulsion is then cooled to about 60° C. with moderate agitation. The base, triethanolamine, is then slowly added to neutralize the acidic Carbomer 940 and the emulsion (pH 6.5) is mixed at moderate speed until uniform. The homogeneous oil-in-water emulsion is then cooled to about 45°-50° C. and the colarant and odorant oil are added followed by cooling to room temperature (about 25° C.) with continued moderate agitation.

The four silicon fluids and other silicone phase ingredients are mixed together in a separate vessel until a uniform silicone phase is attained. The oil-in-water emulsion is slowly added to the silicone phase with stirring until a homogeneous oil-in-water-in-silicone double emulsion in lotion form is attained.

This moisturing lotion is useful for topical application to inhibit damage caused by acute or chronic UV exposure. Use of an amount of lotion sufficient to deposit about 0.5 mg/cm$^2$ of tocopherol sorbate, about 0.5 mg/cm$^2$ of sunscreening agents, and about 0.1 mg/cm$^2$ of naproxen to the skin immediately following UV exposure is appropriate. Substantially similar results are obtained if the lotion is applied to the skin up to 30 minutes after UV exposure or up to 4 hours prior to UV exposure. This lotion may also be applied several times daily, e.g., 2 or 3 times daily, for extended periods of time, i.e., greater than one week, in amounts sufficient to deposit about 0.5 mg/cm$^2$ of tocopherol sorbate, about 0.5 mg/cm$^2$ of sunscreening agents, and about 0.1 mg/cm$^2$ of naproxen to the skin to inhibit damage caused by chronic UV exposure.

Substantially similar results are obtained if the octyl methoxycinnamate and benzophenone-3, are replaced, in whole or in part, with 2-ethylhexyl p-methoxycinnamate, butyl methoxydibenzoyl methane, 2-hydroxy-4-methoxybenzophenone, and mixtures thereof.

Substantially similar results are obtained if the naproxen is replaced, in whole or in part, with hydrocortisome acetate, ibuprofen, flufenamic acid, mefenamic acid, meclofenamic acid, piroxicam, felbinac, 4-(4'-pentyn-3'-one)-2,6-di-t-butylphenol, 4-(5'-hexynoyl)-2,6-di-t-butylphenol, 4-(S)-(—)-3'-methyl-5'-hexynoyl-2,6-di-t-butylphenol, 4-(R)-(+)-3'-methyl-5'-hexynoyl-2,6-di-t-butylphenol, 4-(3',3'-dimethoxypropionyl)-2,6-di-t-butylphenol, Manjistha, Guggal, and mixtures thereof.

EXAMPLE X

A skin conditioning toilet bar is prepared from the following ingredients.

| Component | Percent by Weight of Composition |
| --- | --- |
| Tallow/Coconut Soap (50/50) | 61.61 |
| Water | 10.00 |
| 2-Hydroxypropylglyceryl Ether | 4.00 |
| Sodium Coconut Glyceryl Ether Sulfonate | 8.80 |
| Coconut Fatty Acid (CnFA) | 4.00 |
| Tocopherol Sorbate | 5.00 |
| Perfume | 1.40 |
| NaCl | 1.04 |
| Na$_2$SO$_4$ | 0.34 |
| Na$_4$EDTA | 0.06 |
| TiO$_2$ | 0.20 |
| Jaguar C15 (quar hydroxy propyltrimonium chloride) | 1.00 |
| Merquat 550 (poly quaternium-7) | 1.00 |
| Minors (Colorants, Preservatives, Fillers, etc.) | 1.55 |

The above composition is prepared in the following manner.

Crutching Step

About 127.6 parts of a mix containing: 29.8% water, 52.7% 50/50 tallow/coconut (T/Cn) soap, 16.7% sodium coconut glyceryl ether sulfonate paste, 3.3% coconut free fatty acid (CnFA), 3.1% 2-hydroxypropylglyceryl ether, and 0.2% NaCl are heated to ca. 150°-200° F. (65°-94° C.). About 10.0 parts of the hydrated polymer JAGUAR C-15 are mixed in. The tocopherol sorbate is then added and mixed in.

Vacuum Drying Step

The crutcher mix is vacuum dried at ca. 50 mm Hg absolute pressure to reduce the moisture content of the mix to ca. 10% and to plod this soap into noodles. These noodles are passed through a milling step once.

Amalgamating Step

The once-milled soap noodles are weighed and placed in a batch amalgamator. To about 99.1 parts noodles in the amalgamator are added: 0.20 part TiO$_2$, 1.4 parts perfume, 0.15 part colorant solution, 0.15 part of a solution which contains ca. 40% EDTA. The combined ingredients are mixed thoroughly.

Milling Step

Three-roll soap mills are set up with all rolls at 85°-105° F. (29°-41° C.). The mixture from the amalgamator is passed through the mills several times to obtain a homogeneous mix. This is an intimate mixing step.

Plodding and Stamping Steps

A conventional plodder is set up with the barrel temperature at about 90° F. (32° C.) and the nose temperature at about 110° F. (43° C.). The plodder used is a dual stage twin screw plodder that allows for a vacuum of about 40 to 65 mm Hg between the two stages. The soap log extruded from the plodder is typically round or oblong in cross-section, and is cut into individual plugs. These plugs are then staped on a conventional soap stamping apparatus to yield the finished toilet soap bar.

The use of this toilet bar for cleansing provides a useful means for deposition of tocopherol sorbate to the skin to inhibit damage caused by acute or chronic UV exposure. Use of the toilet bar such that about 0.05 mg/cm$^2$ of tocopherol sorbate is deposited on the skin immediately prior to UV exposure is appropriate. Substantially similar results are obtained if the toilet bar is used up to 4 hours prior to UV exposure or up to 30 minutes after UV exposure.

EXAMPLE XI

Facial Cleanser

A facial cleanser (lathering mousse composition) is prepared from the following ingredients.

| Emulsion Concentrate (A) | Percent by Weight of Composition |
| --- | --- |
| DRO Water[1] | 52.63 |
| 2-Hydroxypropyglyceryl Ether | 15.00 |
| Sodium Glyceryl Ether Sulfonate (90% Coconut/10 Tallow)-50% Active | 12.06 |
| Sodium Lauroyl Sarcosinate - 33% Active | 6.66 |
| PEG 600 | 4.00 |
| Aloe Vera Gel | 1.00 |
| Lexein LP170P (hydrolyzed animal protein) | 1.00 |
| Stearic Acid | 1.00 |

| Emulsion Concentrate (A) | Percent by Weight of Composition |
| --- | --- |
| Citric Acid | 0.30 |
| Tocopherol Sorbate | 5.00 |
| Jaguar C14-S (guar hydroxypropyltrimonium chloride) | 0.25 |
| Perfume | 0.20 |
| FD&C Red Dye #4 | 0.20 |
| Lauryl Alcohol | 0.20 |
| Alkyl Parabens | 0.30 |
| Germall 115 (Imidazolidinyl urea) | 0.10 |
| Na4EDTA | 0.10 |

[1]Water purified by a double reverse osmosis

A-46 Propellant (Isobutane-Propane) (B)

(6.4 g in 100 g concentrate)

The composition is prepared in a single batch process. DRO water is brought to 71.1° C. and the Jaguar polymer is added with agitation. Maintaining agitation, the following ingredients are added sequentially: Sodium glycerol ether sulfonate, Sodium lauroyl sarcosinate, lauryl alcohol, PEG-600, Parabens, EDTA, dye, 2-Hydroxypropylglyceryl ether, stearic acid, Aloe Vera Gel, citric acid and tocopherol sorbate. The mixture is then cooled to 135°-140° F. and the following ingredients are added sequentially with stirring: Lexein, Germall and perfume. The resulting mixture is cooled to room temperature.

Aluminum cans are then filled with the cooled emulsion concentrate. Aerosol activator assemblies are then crimped onto the cans to form a tight seal. Pressurized A-46 Propellant is then pumped into the cans in an amount sufficient to provide a composition consisting of 6% propellant and 94% emulsion concentrate in each can.

Upon activation of the aerosol assembly, the composition is dispensed under pressure in the form of a creamy, foaming mousse which can be applied to the skin for cleansing and as a means for deposition of tocopherol sorbate to the skin to inhibit damage caused by acute or chronic UV exposure. Use of amount of facial cleanser sufficient to deposit about 0.05 mg/cm$^2$ of tocopherol sorbate to the skin immediately prior to UV exposure is appropriate. Substantially similar results are obtained if the cleanser is used up to 4 hours prior to UV exposure or up to 30 minutes after UV exposure.

EXAMPLE XII

A cream soap is prepared by combining the following ingredients as described below.

| Component | Percent by Weight of Composition |
| --- | --- |
| Sodium Lauroyl Glutamate (Acylglutamate LS-11) (28) | 22.00 |
| Sodium Hydrogenated Tallow Glutamate and Cocoyl Glutamate (Acylglutamate GS-11) (28) | 3.00 |
| Polyethylene Glycol 400 | 10.00 |
| Polyethylene Glycol (M.W. 6300) Monostearate | 5.00 |
| Polyoxyethylene (20) Sorbitan Monostearate | 3.00 |
| Tocopherol Sorbate | 5.00 |
| Flufenamic Acid | 5.00 |
| 2-Ethylhexyl Methoxycinnamate | 3.00 |
| Water | 33.50 |
| Glycerin | 10.00 |

| Component | Percent by Weight of Composition |
| --- | --- |
| Fragrance and Preservative | q.s. |

The sodium glutamate, sodium hydrogenated tallow glutamate and cocoyl glutamate, polyethylene glycol, polyethylene glycol monostearate, polyoxyethylene sorbitan monostearate, tocopherol sorbate, flufenamic acid, 2-ethylhexyl methoxycinnamate, and water are dissolved together with heating. The glycerin is added with agitation. The mixture is cooled to about 60° C. and the fragrance and preservative are added. The mixture is cooled to 35° C. with agitation.

The result is a cream soap the use of which for cleansing provides a useful means for deposition of tocopherol sorbate, flufenamic acid, and 2-ethylhexyl methoxycinnamate to the skin to inhibit damage caused by acute or chronic UV exposure. Use of an amount of cream soap sufficient to deposit about 0.05 mg/cm$^2$ of tocopherol sorbate, 0.05 mg/cm$^2$ of the sunscreening agent, and 0.01 mg/cm$^2$ of flufenamic acid to the skin immediately following UV exposure is appropriate. Substantially similar results are obtained if the soap is used up to 30 minutes after UV exposure or up to 4 hours prior to UV exposure.

Substantially similar results are obtained if the 2-ethylhexyl methoxycinnamate is replaced, in whole or in part, with octyl methoxycinnamate, butyl methoxydibenzoylmethane, 2-hydroxy-4-methoxybenzophenone, and mixtures thereof.

Substantially similar results are obtained if the flufenamic acid is replaced, in whole or in part, with hydrocortisone acetate, ibuprofen, naproxen, mefenamic acid, meclofenamic acid, piroxicam, felbinac, 4-(4'-pentyn-3'-one)-2,6-di-t-butylphenol, 4-(5'-hexynoyl)-2,6-di-t-butylphenol, 4-(S)-(−)-3'-methyl-5'-hexynoyl-2,6-di-t-butylphenol, 4-(R)-(+)-3'-methyl-5'-hexynoyl-2,6-di-t-butylphenol, 4-(3',3'-dimethoxypropionyl-2,6-di-t-butylphenol, Manjistha, Guggal, and mixtures thereof.

EXAMPLE XIII

A shampoo composition is made by combining the following components.

| Component | Percent by Weight of Composition |
| --- | --- |
| Ammonium Lauryl Sulfate | 12.0 |
| Ammonium Xylene Sulfonate | 2.2 |
| Ammonium Laureth Sulfate | 4.0 |
| NaCl | 0.5 |
| Tocopherol Sorbate | 5.0 |
| Octyl Dimethyl PABA | 7.0 |
| Water | 68.1 |
| Perfume and Minor Ingredients | 1.2 |

The ammonium lauryl sulfate, ammonium laureth sulfate, and ammonium xylene sulfonate are first mixed together. The tocopherol sorbate and octyl dimethyl PABA and perfume and minor ingredients are added and the resulting mixture is agitated in a Teckmar ® Mill set at 70° for 2 minutes at 70° C.

The resulting shampoo composition is added to hair which has been wetted with water, worked through the hair then rinsed out. This allows for deposition of tocopherol sorbate and octyl dimethyl PABA to the scalp to inhibit damage caused by acute or chronic UV exposure. Use of an amount of shampoo sufficient to deposit about 0.05 mg/cm$^2$ of tocopherol sorbate and 0.05 mg/cm$^2$ of sunscreening agent to the scalp immediately following UV exposure is appropriate. Substantially similar results are obtained if the shampoo is used up to 30 minutes after or up to 4 hours prior to UV exposure.

Substantially similar results are obtained if the octyl dimethyl PABA is replaced, in whole or in part, with 2-ethylhexyl methoxycinnamate, butyl methoxydibenzoylmethane, 2-hydroxy-4-methoxybenzophenone, octyl methoxycinnamate, and mixtures thereof.

Substantially similar results are obtained if the flufenamic acid is replaced, in whole or in part, with hydrocortisone acetate, ibuprofen, naproxen, mefenamic acid, meclofenamic acid, piroxicam, felbinac, 4-(4'-pentyl-3'-one)-2,6-di-t-butylphenol, 4-(5'-hexynoyl)-2,6-di-t-butylphenol, 4-(S)-(−)-3'-methyl-5'-hexynoyl-2,6-di-t-butylphenol, 4-(R)-(+)-3'-methyl-5'-hexynoyl-2,6-di-t-butylphenol, 4-(3',3'-dimethoxypropionyl)-2,6-di-t-butylphenol, Manjistha, Guggal, and mixtures thereof.

What is claimed is:

1. A composition useful for topical application comprising a safe and photoprotectively effective amount of tocopherol sorbate and a safe and effective amount of a topical carrier wherein the the tocopherol sorbate is present in an amount of not more than about 25% weight.

2. The composition of claim 1 which comprises from about 1% to about 10% of tocopherol sorbate.

3. The composition of claim 2 which comprises from about 1% to about 5% of tocopherol sorbate.

4. The composition of claim 2 which comprises from about 85% to about 99% of the carrier.

5. The composition of claim 4 which is in the form of a solution.

6. The composition of claim 5 which additionally comprises a thickening agent in an amount sufficient to form a gel.

7. The composition of claim 5 which additiionally comprises a propellant in an amount sufficient to form an aerosol spray.

8. The composition of claim 4 wherein the carrier comprises an emollient.

9. The composition of claim 8 wherein the emollient is selected from the group consisting of hydrocarbon oils and waxes, silicone oils, triglyceride esters, acetoglyceride esters, ethoxylated glycerides, alkyl esters of fatty acids, alkenyl esters of fatty acids, fatty acids, fatty alcohols, fatty alcohol ethers, fatty acid esters of ethoxylated fatty alcohols, ether-esters, lanolin and its derivatives, polyhydric alcohols, and polyether derivatives, polyhydric alcohol esters, wax esters, beeswax derivatives, vegetable waxes, phospholipids, sterols, amides, and mixtures thereof.

10. The composition of claim 8 wherein the emollient is glycerol.

11. The composition of claim 8 containing from about 1% to about 10% by weight of an emollient which comprises a propoxylated glycerol derivative having the formula:

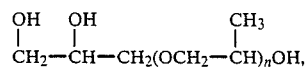

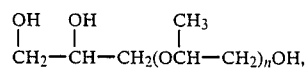

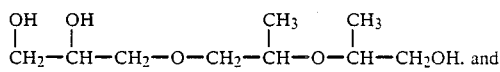

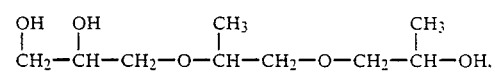

wherein n=1 or 2, and mixtures thereof.

12. The composition of claim 4 which is in the form of an emulsion.

13. The composition of claim 12 wherein the emulsion comprises from about 1% to about 10% by weight of an emulsifier.

14. The composition of claim 13 wherein the emulsifier is an organic nonionic surfactant.

15. The composition of claim 12 which is formulated as a lotion.

16. The composition of claim 12 which is formulated as a cream.

17. The composition of claim 4 which is formulated as a cosmetic foundation.

18. The composition of claim 4 which is formulated as a lipstick.

19. A skin cleaning composition of claim 1 wherein the carrier comprises from about 5% to about 80% of a cosmetically-acceptable surfactant.

20. The composition of claim 19 wherein the surfactant is anionic and is selected from the group consisting of soaps, alkyl glycerol ether sulfonates and mixtures thereof.

21. The composition of claim 19 which is in the form of a bar soap.

22. The composition of claim 19 which is in the form of a liquid soap.

23. The composition of claim 19 which is in the form of a paste.

24. The composition of claim 19 which is in the form of a mousse.

25. The composition of claim 4 wherein the carrier comprises an oil-in-water-in-silicone fluid emulsion composition comprising:
   (a) from about 15% to about 90% by weight of the emulsion composition of a silicone fluid continuous phase consisting essentially of at least one liquid organopolysiloxane;
   (b) from about 30% to about 80% by weight of the emulsion composition of an aqueous discontinuous phase comprising an oil-in-water emulsion of a cosmetically-acceptable oily liquid non-particulate phase dispersed in an aqueous phase; and
   (c) from about 0.5% to about 5% by weight of the emulsion composition of an effective dispersing amount of dimethicone copolyol for dispersing (b) in (a).

26. The composition of claim 4 which additionally comprises from about 0.25% to about 3% of an ethylene acrylic acid copolymer having the formula

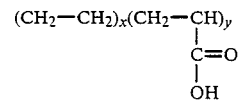

wherein the ratio of x:y is from about 1:9 to about 1:24 and the molecular weight of the copolymer is from about 3500 to about 4500.

27. The composition of claim 4 which additionally comprises a safe and effective amount of a penetration enhancer.

28. The composition of claim 4 which additionally comprises a safe and photoprotectively effective amount of a sunscreening agent.

29. The composition of claim 28 which comprises from about 1% to about 10% of the sunscreening agent.

30. The composition of claim 29 wherein the sunscreening agent is selected from the group consisting of 2-ethylhexyl p-methoxycinnamate, butyl methoxydibenzoylmethane, 2-hydroxy-4-methoxybenzophenone, octyl dimethyl p-aminobenzoic acid, the 4-N,N-(2-ethylhexyl)methylaminobenzoic acid ester of 2,4-dihydroxybenzophenone, the N,N-di-(2-ethylhexyl)-4-aminobenzoic acid ester of 4-hydroxydibenzoylmethane, the 4-N,N-(2-ethylhexyl)methylaminobenzoic acid ester of 4-hydroxy- di-benzoylmethane, the 4-N,N-(2-ethylhexyl)methylaminobenzoic acid ester of 2-hydroxy-4-(2-hydroxyethoxy) benzophenone, the 4-N,N-(2-ethylhexyl)methylaminobenzoic acid ester of 4-(2-hydroxy-ethoxy)dibenzoylmethane, the N-N-di-(2-ethylhexyl)-4-aminobenzoic acid ester of 2-hydroxy-4-(2-hydroxyethoxy)benzophenone, the N,N-di(2-ethylhexyl)-4-aminobenzoic acid ester of 4-(2-hydroxyethoxy)dibenzoylmethane and mixtures thereof.

31. The composition of claim 26 which additionally comprises a sunscreening agent selected from the group consisting of 2-ethylhexyl p-methoxycinnamate, butyl methoxydibenzoylmethane, 2-hydroxy-4-methoxybenzophenone, octyldimethyl p-aminobenzoic acid and mixtures thereof.

32. A method of inhibiting the deleterious effects of ultraviolet light exposure to skin comprising applying a safe and photoprotectively effective amount of tocopherol sorbate to the skin in conjunction with exposing the skin to ultraviolet light.

33. The method of claim 32 wherein from about 0.01 mg/cm$^2$ to about 1.0 mg/cm$^2$ of tocopherol sorbate is applied to the skin.

34. The method of claim 33 wherein from about 0.05 mg/cm$^2$ to about 0.5 mg/cm$^2$ of tocopherol sorbate is applied to the skin.

35. A method of inhibiting the deleterious effects of ultraviolet exposure to skin comprising applying a safe and photoprotectively effective amount of tocopherol sorbate and a safe and photoprotectively effective amount of a sunscreening agent to the skin simultaneously in conjunction with UV exposure.

36. The method of claim 35 wherein from about 0.01 mg/cm$^2$ to about 1.0 mg/cm$^2$ tocopherol sorbate and from about 0.01 mg/cm$^2$ to about 1.0 mg/cm$^2$ of the sunscreening agent is applied to the skin.

37. The method of claim 36 wherein from about 0.05 mg/cm$^2$ to about 0.5 mg/cm$^2$ tocopherol sorbate and from about 0.05 mg/cm$^2$ to about 0.5 mg/cm$^2$ of the sunscreening agent is applied to the skin.

38. The method of claim 37 wherein the sunscreening agent is selected from the group consisting of 2-ethylhexyl p-methoxycinnamate, butyl methoxydibenzoylmethane, 2-hydroxy-4-methoxybenzophenone, octyl dimethyl p-aminobenzoic acid, the 4-N,N-(2-ethylhexyl)methylaminobenzoic acid ester of 2,4-dihydroxybenzophenone, the N,N-di-(2-ethylhexyl)-4-aminobenzoic acid ester of 4-hydroxydibenzoylmethane, the 4-N,N-(2-ethylhexyl)methylaminobenzoic acid ester of 4-hydroxydi-benzoylmethane, the 4-N,N-(2-ethylhexyl)methylaminobenzoic acid ester of 2-hydroxy-4-(2-hydroxyethoxy)benzophenone, the 4-N,N-(2-ethylhexyl)methylaminobenzoic acid ester of 4-(2-hydroxyethoxy)dibenzoylmethane, the N-N-di-(2-ethylhexyl)-4-aminobenzoic acid ester of 2-hydroxy-4-(2-hydroxyethoxy)benzophenone, the N,N-di-(2-ethylhexyl)-4-aminobenzoic acid ester of 4-(2-hydroxyethoxy)dibenzoylmethane and mixtures thereof.

39. The method of claim 32 wherein the tocopherol sorbate is applied to the skin up to about 4 hours prior to UV exposure.

40. The method of claim 35 wherein the tocopherol sorbate and the sunscreening agent are applied to the skin up to about 4 hours prior to UV exposure.

* * * * *

UNITED STATES PATENT AND TRADEMARK OFFICE
CERTIFICATE OF CORRECTION

PATENT NO. : 4,847,072

DATED : July 11, 1989

INVENTOR(S) : Donald L. Bissett and Rodney D. Bush

It is certified that error appears in the above-identified patent and that said Letters Patent is hereby corrected as shown below:

Column 3, line 37, "compositions" should be --composition--.

Column 3, line 62, "ibuprofen)" should be --(ibuprofen)--.

Column 5, line 32, "perhpas" should be --perhaps--.

Column 6, line 57, "cichlorotetrafluoroethane" should be --dichlorotetrafluoroethane--.

Column 11, line 33, "supra" should be --*supra*--.

Column 15, line 67, "radicla" should be --radical--.

Column 16, line 12, "dodceylamine" should be --dodecylamine--.

Column 18, line 1, "Schmidit" should be --Schmidt--.

Column 23, line 21, "inventin" should be --invention--.

Column 25, line 4, "active" should be --actives--.

Column 28, line 29, "up 4 hours" should be --up to 4 hours--.

UNITED STATES PATENT AND TRADEMARK OFFICE
CERTIFICATE OF CORRECTION

PATENT NO. : 4,847,072

DATED : July 11, 1989

INVENTOR(S) : Donald L. Bissett, et al

It is certified that error appears in the above-identified patent and that said Letters Patent is hereby corrected as shown below:

Column 33, lines 36-37, "hydrocorti some" should be --hydrocortisone--.

Column 36, line 64, "Mill set at 70° for 2 minutes at 70°C" should be --Mill set at 70 for 2 minutes at 70°C--.

Signed and Sealed this

Twenty-third Day of October, 1990

Attest:

HARRY F. MANBECK, JR.

*Attesting Officer*     *Commissioner of Patents and Trademarks*